US007751529B2

(12) United States Patent
Ohara

(10) Patent No.: US 7,751,529 B2
(45) Date of Patent: Jul. 6, 2010

(54) RADIATION IMAGE RADIOGRAPHING SYSTEM

(75) Inventor: Hiromu Ohara, Tokyo (JP)

(73) Assignee: Konica Minolta Medical & Graphic, Inc. (JP)

( * ) Notice: Subject to any disclaimer, the term of this patent is extended or adjusted under 35 U.S.C. 154(b) by 153 days.

(21) Appl. No.: 11/908,270

(22) PCT Filed: Feb. 14, 2006

(86) PCT No.: PCT/JP2006/302500

§ 371 (c)(1), (2), (4) Date: Sep. 10, 2007

(87) PCT Pub. No.: WO2006/095538

PCT Pub. Date: Sep. 14, 2006

(65) Prior Publication Data

US 2009/0022276 A1 Jan. 22, 2009

(30) Foreign Application Priority Data

Mar. 10, 2005 (JP) ............................ 2005-068118

(51) Int. Cl.
*H05G 1/58* (2006.01)

(52) U.S. Cl. ......................... 378/116; 378/91; 378/98.8

(58) Field of Classification Search .................. 378/91, 378/98.8, 114–116
See application file for complete search history.

(56) References Cited

U.S. PATENT DOCUMENTS 6,431,751 B1 * 8/2002 Everett et al. ............... 378/197
7,239,685 B2 * 7/2007 Petrick et al. ............... 378/116
2005/0043620 A1 2/2005 Fallows et al.

FOREIGN PATENT DOCUMENTS

| | | | |
|---|---|---|---|
| EP | 1 418 753 | A2 | 5/2004 |
| FR | 2 699 805 | A1 | 7/1994 |
| JP | 6-342099 | | 12/1994 |
| JP | 8-273888 | | 10/1996 |
| JP | 2000-245719 | | 9/2000 |
| JP | 2001-149358 | | 6/2001 |
| JP | 2002-336225 | | 11/2002 |
| WO | 98/15227 | A1 | 4/1998 |
| WO | 2005/096944 | A1 | 10/2005 |

OTHER PUBLICATIONS

European Search Report for European Application No. 06713641. 6—2319/1857048 PCT/JP2006302500 dated Mar. 31, 2009 with English Translation.

International Search Report for International Application No. PCT/JP2006/302500 dated Mar. 20, 2006.

* cited by examiner

*Primary Examiner*—Jurie Yun
(74) *Attorney, Agent, or Firm*—Cantor Colburn LLP

(57) ABSTRACT

A radiation image radiographing system 1 including a radiation image detector 5 detecting a radiated radiation to obtain image information, a console 6 operating the radiation image detector 5, and associating means for performing the association with the console 6 operating the radiation image detector 5 at the time of radiography, wherein the radiation image detector 5 includes a power supplying means 21 controlling the state of power supply according to the operation status of the console 6 associated by the associating means.

11 Claims, 11 Drawing Sheets

1 2 6 6 7 10 8 12 4 6 3 13 9 5 5 11 34

1
2
3
4
5
6
7
8
9
10
11
12
13
34

101
102
103
104
105
106
107a
107b
107c
108
109
111
112
126
128
150

RADIATION IMAGE RADIOGRAPHING SYSTEM

CROSS REFERENCE TO RELATED APPLICATIONS

This is a U.S. national stage of application No. PCT/JP2006/302500, filed on 14 Feb. 2006. Priority under 35 U.S.C. §119(a) and 35 U.S.C. §365(b) is claimed from Japanese Application No. 2005-068118, filed 10 Mar. 2005, the disclosure of which is also incorporated herein by reference.

BACKGROUND OF THE INVENTION

1. Technical Field

The present invention relates to a radiation image radiographing system, and more particularly to a radiation image radiographing system for radiographing a radiation image represented by an X-ray image.

2. Background Art

A radiation image obtained by radiating a radiation, such as an X ray, to a subject and by detecting an intensity distribution of the radiation that has transmitted the subject has been widely used in a medical diagnosis. In recent years, a radiation image radiographing apparatus using a flat panel detector (FPD) which detects a radiation as radiation image information by converting the detected radiation into electric energy at the time of radiography, has been developed.

In recent years, a cassette shaped FPD housing a FPD in a cassette in order to improve the transportability and handling property of the FPD has been also developed (see, for example, Patent Document 1). In particular, a cassette shaped FPD wirelessly communicating with a console controlling the cassette shaped FPD in order to make the most of the conveyance property of the cassette shaped FPD has been proposed.

Now, a conventional FPD is associated with a radiographing system having a connecting port connecting a FPD at the time of radiography by being connected (see Patent Document 2).

[Patent Document 1] Japanese Patent Application Laid-Open Publication No. Hei 6-342099

[Patent Document 2] Japanese Patent Application Laid-Open Publication No. 2002-336225

However, the conventional FPD only receives system information for the image correction and the image treatment of the associated radiographing system thereto, but does not change its own operation state according to the operation status of the console. Moreover, it is necessary to command the start-up of the FPD anew through the FPD itself or the console at the time of using the FPD.

In particular, in the case of urgent radiography, it is needed to reduce the trouble and time of operations before performing radiography as less as possible. Moreover, a radiation image detector that is not started is used by mistake, and patients are sometimes obliged to receive re-radiography. A patient is sometimes exposed to unnecessary radiation by mistakes in operation.

It is an object of the present invention to improve the operationality at the time of radiography.

SUMMARY OF THE INVENTION

According to a first aspect of the invention, a radiation image radiographing system comprises:

a radiation image detector to detect an applied radiation to obtain image information;

a console for operating the radiation image detector; and an associating section to perform association with the console for operating the radiation image detector at radiographing, wherein the radiation image detector includes a power supplying section to control a state of power supply according to an operating status of the console associated by the associating section.

Preferably, a plurality of the consoles are comprised, wherein the associating section performs the association with one of the plurality of consoles.

Preferably, the radiation image detector, as the state of power supply, includes:

a state of being capable of radiography with power consumption necessary for radiographing:

a state of waiting radiography with lower power consumption than in the state of being capable of radiography; and a state of preparing waiting with lower power consumption than in the state of waiting radiography.

Preferably, the power supplying section changes the state of power supply to the state of being capable of radiography or the state of waiting radiography when it is detected that the console is in operation.

Preferably, the power supplying section changes the state of power supply to the state of preparing waiting when it is detected that the console is in a halt condition.

Preferably, the power supplying section changes the state of power supply to the state of waiting radiography after a lapse of predetermined time from changing the state of power supply to the state of being capable of radiography, when any radiography instructions has been received from the console.

Preferably, the console includes an informing section to inform the state of power supply of the radiation image detector.

Preferably, the radiation image detector is a cassette type flat panel detector.

Preferably, the radiation image detector includes: detecting section to detect the progress of an operation based on an instruction from the associate console; and a control section to allow the power supplying section to control the state of power supply when completion of the operation according to the instruction of the associated console is detected.

Preferably, releasing section to release the association with the console associated by the associating section is further comprised, wherein the control section allows the releasing section to release the association with the associated console when the detecting section detects the completion of the operation according to an instruction of the associated console.

Preferably, a plurality of the consoles are comprised, wherein the radiation image detector is associated with one of the plurality of consoles, and the control section enables the association with a next console when the releasing section releases the association with the associated console.

According to the first aspect of the present invention, the radiation image detector can automatically control the state of power supply according to the operation status of the associated console. Consequently, the troublesome operations for starting the radiation image detector and the waiting time for the start-up can be removed when urgent radiography is desired, and the operationality of radiography can be improved. Moreover, it can be prevented that unnecessary exposure of radiations of a patient caused by using an unstarted radiation image detector by mistake.

In particular, if the state of power supply is controlled so as to suppress the power consumption of the radiation image detector when the console has not started, then the radiation image detector can be operated in its power saving mode, in which the power consumption of the radiation image detector can be suppressed, when the console has not started, that is, when no radiography is performed, and useless power consumption can be reduced.

Moreover, because the radiation image detector can be associated with one of the plurality of consoles, which is associated by the associating means, the radiation image detector can control the state of power supply according to the operation status of the specific console associated by the associating means.

Moreover, because the radiation image detector can set its states of power supply of different power consumption quantities, the radiation image detector can automatically change the state of power supply according to the operation status of the associated console.

Moreover, because the power supplying means sets its state in the state of being capable of radiography or the state of waiting radiography among the three power supplying states provided in the radiation image detector in the situation in which there is the possibility of performing radiography, such as the situation in which the console has started, the radiation image detector performs radiography, or can put the radiation image detector 5 on standby in the state in which power consumption quantity is lower than that at the time of radiography to reduce useless power consumption, although no radiography is performed, in the situation in which there is the possibility of performing radiography. In particular, if the state of waiting radiography is a state capable of quickly shifting to the state of being capable of radiography, then radiography can be quickly performed at the time of start-up of the console. Moreover, the forgetting of turning on the power source of the radiation image detector can be also prevented.

Moreover, in the situation in which the console has not started and it is expected that there is no possibility of performing radiography, the radiation image detector sets the power supplying state in the state of preparing waiting, which is the state of consuming electric power least among the three power supplying states included in the radiation image detector, with the power supplying means. Consequently, in the situation in which it is expected that there is no possibility of performing radiography, it is possible to set the state of power supply in the state of preparing waiting to reduce useless power consumption as much as possible. Moreover, it is also possible to prevent the forgetting of turning off the power source of the radiation image detector.

Moreover, even if the console has started, the power supplying means makes the state of power supply to the state of waiting radiography when no radiography instruction is transmitted from the console in the predetermined time from the state of power supply has been changed to the state of being capable of radiography. Consequently, in the situation in which there is no possibility of immediately performing radiography but it is expected that radiography will be performed, the radiation image detector can perform quick radiography while reducing useless power consumption as much as possible by changing the state of power supply to the state of waiting radiography.

Moreover, because the console can inform of the state of power supply through the informing section, a radiological technician can select a radiation image detector that will be used for radiography from that time, or can cope with the situation by giving the next instruction to the radiation image detector during radiography or the like on the basis of the information.

Moreover, the radiation image radiographing system can be easily carried independently of radiographing places, and flexibility of the radiography is improved. Consequently, the operationality at the time of radiography can be improved.

Moreover, the radiation image detector detects the progress of the operation based on an instruction of the associated console with detecting means, and can make the power supplying means control the state of power supply when the radiation image detector detects the completion of the operation based on the instruction of the associated console. Consequently, the radiation image detector can control the state of power supply according to the progress of the operation based on the instruction of the associated console with the associating means.

Moreover, the radiation image detector includes the releasing means for releasing the association with the associated console by the associating means, and can make the releasing means release the association with the associated console when the radiation image detector detects the completion of the operation based on an instruction of the associated console with the detecting means. Consequently, the radiation image detector can be controlled so as to release the association with the associated console when the operation based on the instruction of the associated console has been completed.

Moreover, the radiation image detector is associated with one of the plurality of consoles which one is associated with the radiation image detector by the associating means, and includes the plurality of consoles. The radiation image detector can be associated with another next console when the association with the associated console is released by the releasing means. Consequently, the radiation image detector can be controlled so as to be enabled to be associated with the next console when the association with the associated specific console is released by the associating means.

DETAILED DESCRIPTION OF PREFERRED EMBODIMENT

In the following, an embodiment according to the present invention will be described with reference to FIGS. 1-6. However, the present invention is not limited to the shown examples.

First Embodiment

Figure 1:
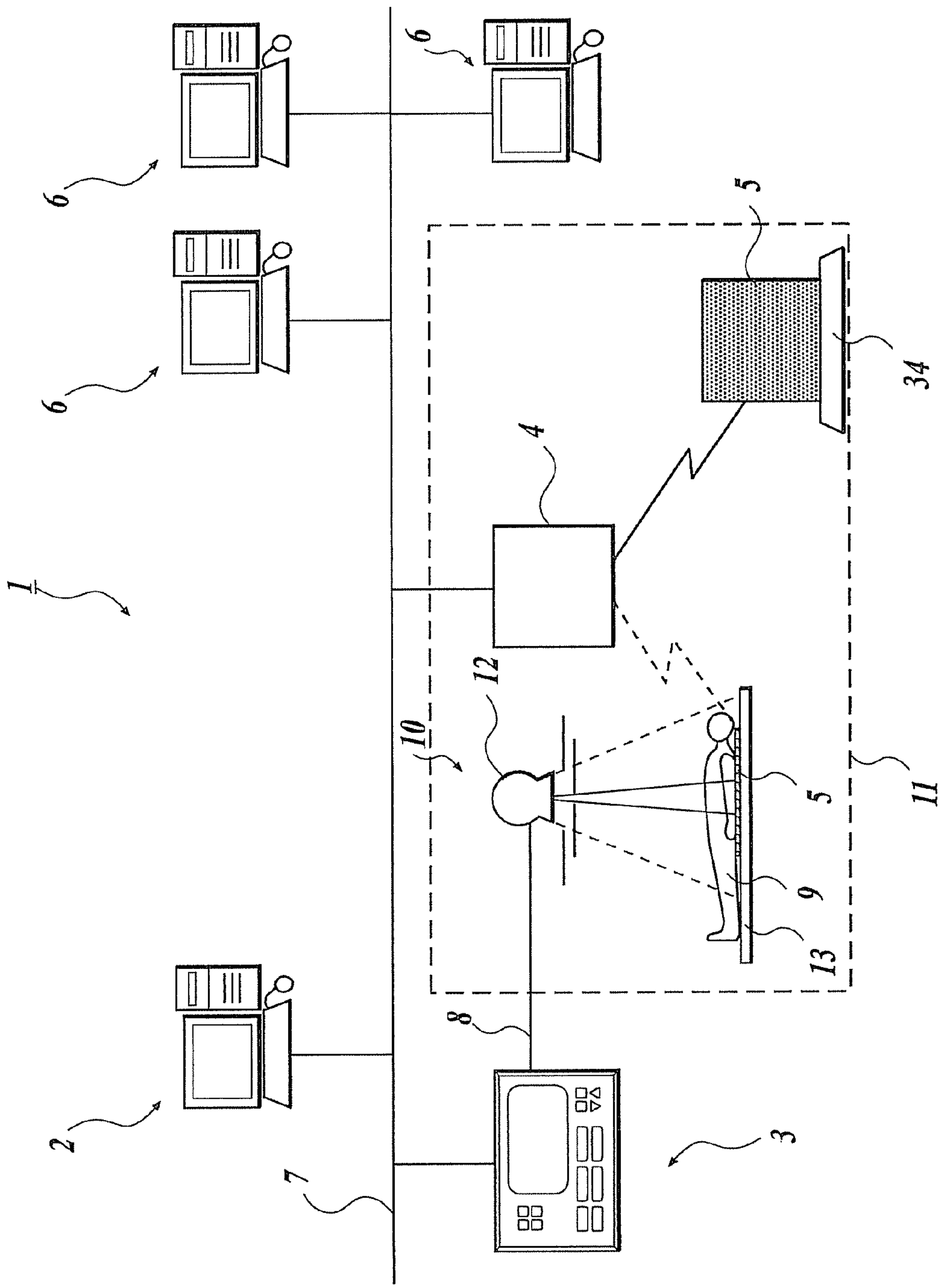
FIG. 1 is a view showing the schematic configuration illustrating a first embodiment of a radiation image radiographing system according to the present invention.

First, a first embodiment is described. FIG. 1 is a view showing the schematic configuration of an embodiment of a radiation image radiographing system to which a radiation image detector according to the present invention is applied.

The radiation image radiographing system 1 according to the present embodiment is, for example, a system applied to radiation image radiography performed in a hospital. As shown in the FIG. 1, a server 2 managing various kinds of information and the like pertaining to radiography and patients, a radiation radiating operation apparatus 3 performing the operations pertaining to radiation irradiation, a base station 4 for performing communication by a wireless communication system, such as wireless local area network (LAN), and a plurality of consoles 6, 6 . . . controlling a radiation image detector 5 and performing image processing of a radiation image radiation image detected by the detector 5 are mutually connected through a network 7. A radiation radiating apparatus 10 radiating a radiation to a patient who is a subject 9 to perform radiography of a radiation image is connected to the radiation radiating operation apparatus 3 through a cable 8. The radiation radiating apparatus 10 and the radiation image detector 5 are, for example, installed in one radiographing room 11 by one severally, and the radiation image radiographing system 1 is configured to be able to obtain radiation image information by operating the radiation radiating apparatus 10 with the radiation radiating operation apparatus 3 to detect a radiation image with the radiation image detector 5. Incidentally, a plurality of radiation image detectors 5 may be installed in one radiographing room 11, and the number of the radiographing rooms 11 is not limited to the one shown in the drawing, but a plurality of radiographing rooms 11 may be installed. Moreover, because the simple reflections of the operation statuses of newly associated consoles 6 suffice for the radiation image detector 5, the consoles 6 are not necessarily connected to the network 7. However, it is necessary for the radiation image detector 5 to be in an environment enabling the performance of the transmission and the reception of various signals, such as mutually performing the transmission and the reception of wireless signals with the consoles 6.

Now, the network 7 may be a communication line dedicated for the system, but it is more preferable that the network 7 is the existing lines such as Ethernet (registered trademark) from the reasons of reducing the flexibility of the system configuration and the like. Incidentally, the radiation image detector and the radiography operation apparatus (both of them are not shown) of another radiographing room 40 may be connected to the network 7 through a base station 43.

The radiation radiating operation apparatus 3 includes an input operating section formed of an operation panel and the like to input a signal, such as the radiography conditions of a tube voltage, an irradiation dose (mAs), and the like, for operating the radiation radiating apparatus 10; a display section displaying the information of the radiography conditions and the like, various instructions, and the like; a power supply section supplying electric power to the radiation radiating apparatus 10; and the like (all of them are not shown).

The radiation radiating apparatus 10 is disposed in the inner part of the radiographing room 11, and includes a radiation source 12 radiating a radiation. The radiation radiating apparatus 10 is configured to radiate a radiation from the radiation source 12 under the conditions of a tube voltage and an irradiation dose that are set by the radiation radiating operation apparatus 3. For example, a radiation tube is used as the radiation source 12, and the radiation tube is configured to generate a radiation by accelerating electrons produced by thermal excitation to make the accelerated electrons collide with the cathode of the radiation tube.

Next, the consoles 6 are described.

Figure 2:
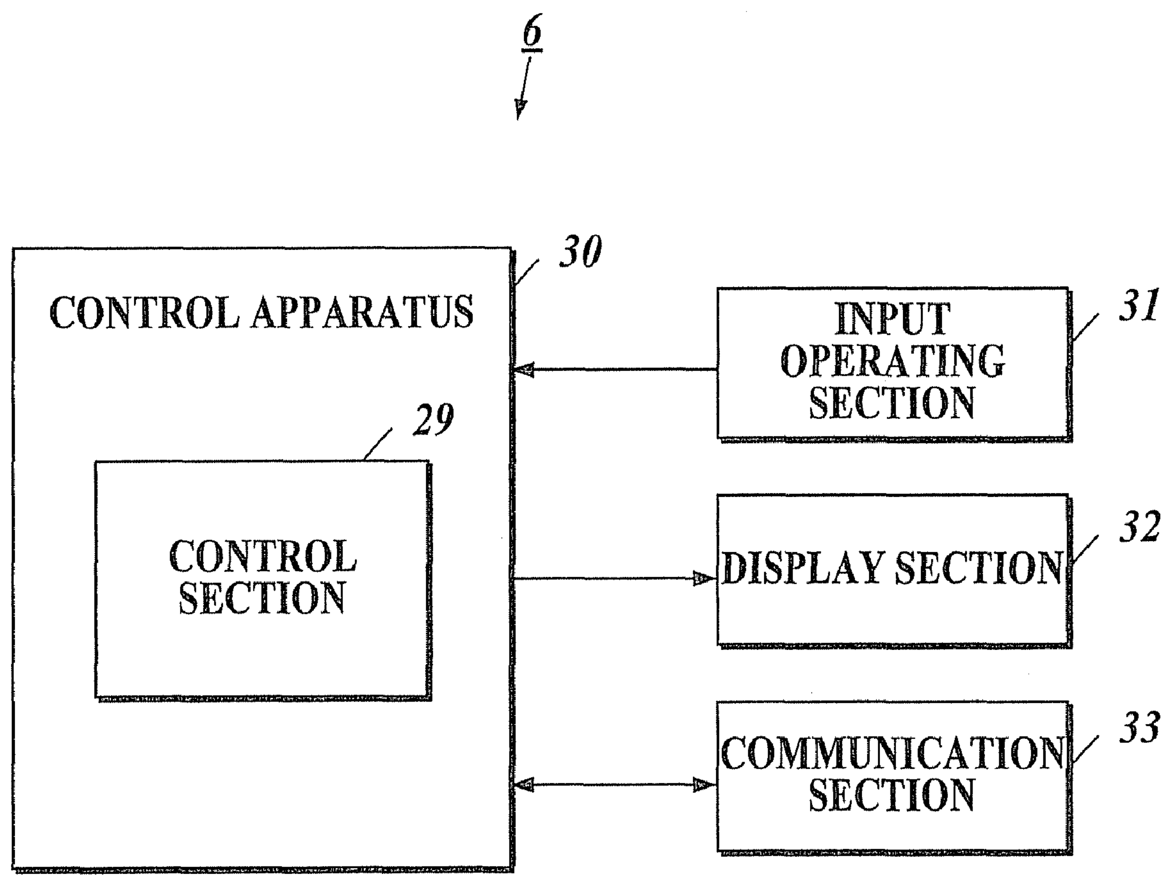
FIG. 2 is a block diagram showing the configuration of the principal part of a console constituting the radiation image radiographing system of the FIG. 1.

As shown in FIG. 2, each of the consoles 6 includes a control apparatus 30 having a control section 29 composed of, for example, a general purpose central processing unit (CPU), a read only memory (ROM), a random access memory (RAM), and the like (all of which are not shown), and the control section 29 is configured to read a predetermined program stored in the ROM, and to expand the read program into the working area of the RAM. And the CPU executes various kinds of processing in accordance with the program. Incidentally, identification information (such as an ID, a bar code, and the like) for distinguishing the plurality of consoles 6 on the network 7 is given to each of the consoles 6.

Moreover, each of the consoles 6 includes an input operating section 31 inputting various instructions and the like; a display section 32 as an informing section displaying images, various messages, and the like; a communication section 33 performing the transmission and the reception of various signals with an external apparatus, such as the radiation image detector 5, and the like.

The input operating section 31 is composed of, for example, an operation panel, a keyboard, a mouse, and the like, and outputs a depression signal of a key operated by depression on the operation panel or the keyboard and an operation signal by the mouse to the control section 29 as an input instruction.

In the input operating section 31, for example, the identification information (such as the ID and the bar code) of the radiation image detector 5 to be used in the radiographing room 11 is input as an association instruction among input instructions. Incidentally, the identification information of the radiation image detector 5 to be input may include a plurality of pieces of information. Moreover, the input of the information may not be performed from the console 6 managing the radiographing room 11 in which the radiation image detector 5 is used. Moreover, the identification information of both of the radiation image detector 5, which are used in the radiographing room 11, and the console 6 may be input as the association instruction.

Moreover, in the input operating section 31, as a radiography reserving instruction, the patient to be radiographed next may be selected in a radiography list displayed on the display section 32, and any radiation image detector 5 among the specific radiation image detectors 5 on the network 7 to be used for the patient, that is, the radiation image detectors 5 on the network 7 associated with itself.

Moreover, in the input operating section 31, as a radiography instruction, an instruction of performing radiation irradiation is input. Incidentally, the radiography instruction may be input from the radiation radiating operation apparatus 3.

Moreover, in the input operating section 31, as a start-up instruction and a halt instruction, instructions of starting and stopping the console are input.

The display section 32 is composed of, for example, a cathode ray tube (CRT), a liquid crystal display (LCD), or the like, and displays various screens in accordance with the instructions of display signals from the control section 29. In the display section 32, for example, a radiography list sent from an external device on the network 7, such as the server 2, and various kinds of information pertaining to the radiation image detector 5 on the network 7 associated with the console 6 can be displayed. Incidentally, in the radiography list, patient information necessary for performing radiography, such as the name, the sex, the radiography portion, and the like, of the patient scheduled to be radiographed is listed.

The communication section 33 performs the communication of various kinds of information with the external devices on the network 7, such as the radiation image detector 5 and the server 2, through the base station 4 by a wireless communication system, such as a wireless LAN.

An input instruction from the input operating section 31 and the information received from the outside through the communication section 33 are input into the control section 29, and the control section 29 performs predetermined processing of the input instruction or information.

For example, when an association instruction is input with the input operation section 31, the control section 29 performs the association of the radiation image detector 5 the identification information of which has been input with the input operating section 31 with the console 6. Incidentally, if only the identification information of the radiation image detector 5 used in the radiographing room 11 has been input with the input operation section 31, the control section 29 performs the association of the radiation image detector 5 to which the input identification information is given with the console 6.

Moreover, when an association instruction input with the input operating section 31, the control section 29 adds a radiation image detector 5 to be associated at each time it occurs.

Moreover, when a radiography reserving instruction is input with the input operating section 31, the control section 29 selects the radiation image detector 5 selected by the input operating section 31 among the radiation image detectors 5 that have been associated the console 6 itself. That is, the radiography reserving instruction associates a patient to be radiographed with the radiation image detector 5 to be used for the patient by selecting the radiation image detector 5 to be used for the patient among the radiation image detectors 5 associated to the patient to be radiographed.

Moreover, when a certain radiation image detector 5 is selected on the basis of the input of a radiography reserving instruction, the control section 29 transmits a radiography reserving instruction signal to the communication section 24 of the radiation image detector 5 having the selected identification information through the communication section 33.

Moreover, when a radiography instruction is input with the input operating section 31, the control section 29 transmits a radiography instruction signal to the communication section 24 of the radiation image detector 5 through the communication section 33.

Moreover, when an halt instruction is input with the input operating section 31, the control section 29 transmits an halt instruction signal to the communication section 24 of the associated radiation image detector 5 through the communication section 33, and after that the control section 29 stops the operation of the console 6, so that the console 6 becomes the state of being powered off (with the power source turned off). On the other hand, when a start-up instruction is input with the input operating section 31, the control section 29 begins the start-up of the console 6, and the console 6 becomes the state of being powered on (with the power source turned on). The console 6 transmits a start-up instruction signal to the communication section 24 of the associated radiation image detector 5 through the communication section 33.

Moreover, when a confirmation signal is input from the radiation image detector 5 though the communication section 33, the control section 29 sends an operation status signal as a reply, which is the information indicating its own operation status, through the communication section 33.

Moreover, when an image signal detected by the radiation image detector 5 is input through the communication section 33, the control section 29 performs predetermined image processing.

Moreover, the control section 29 is configured to make the display section 32 display information, instructions, or the like, input with the communication section 33 and the input operating section 31, and makes the display section 32 display various kinds of information pertaining to the radiation image detector 5 associated with the console 6 besides the aforesaid radiography list and the like. As the various kinds of information pertaining to the radiation image detector 5, for example, the image signal from the radiation image detector 5 associated with the console 6 itself, a radiation image based on an operation state signal, an operation state, and the like, can be cited. Incidentally, as a radiation image to be displayed on the display section 32, reduced image information having an information quantity smaller than that of the original image information thereof, such as the radiation image information to which image processing has been performed and a thumbnail image, may be used.

Next, the radiation image detector 5 is described.

The radiation image detector 5 detects a radiation radiated from the radiation source 12 of the radiation radiating apparatus 10 to have transmitted the subject 9, and obtains a radiation image. The radiation image detector 5 is disposed in a radiation range of radiations radiated from the radiation source 12 to be used at the performance of radiography. Incidentally, although the radiation image detector 5 is disposed between the subject 9 and a bed 13 placing the subject 9 thereon in FIG. 1, the position where the radiation image detector 5 is disposed is not limited to the position. For example, a detector installing port (not shown) installing the radiation image detector 5 is formed below the bed, and the radiation image detector 5 may be installed in the detector installing port.

In the following, the structure of the radiation image detector 5 is described using FIGS. 3-6.

Figure 3:
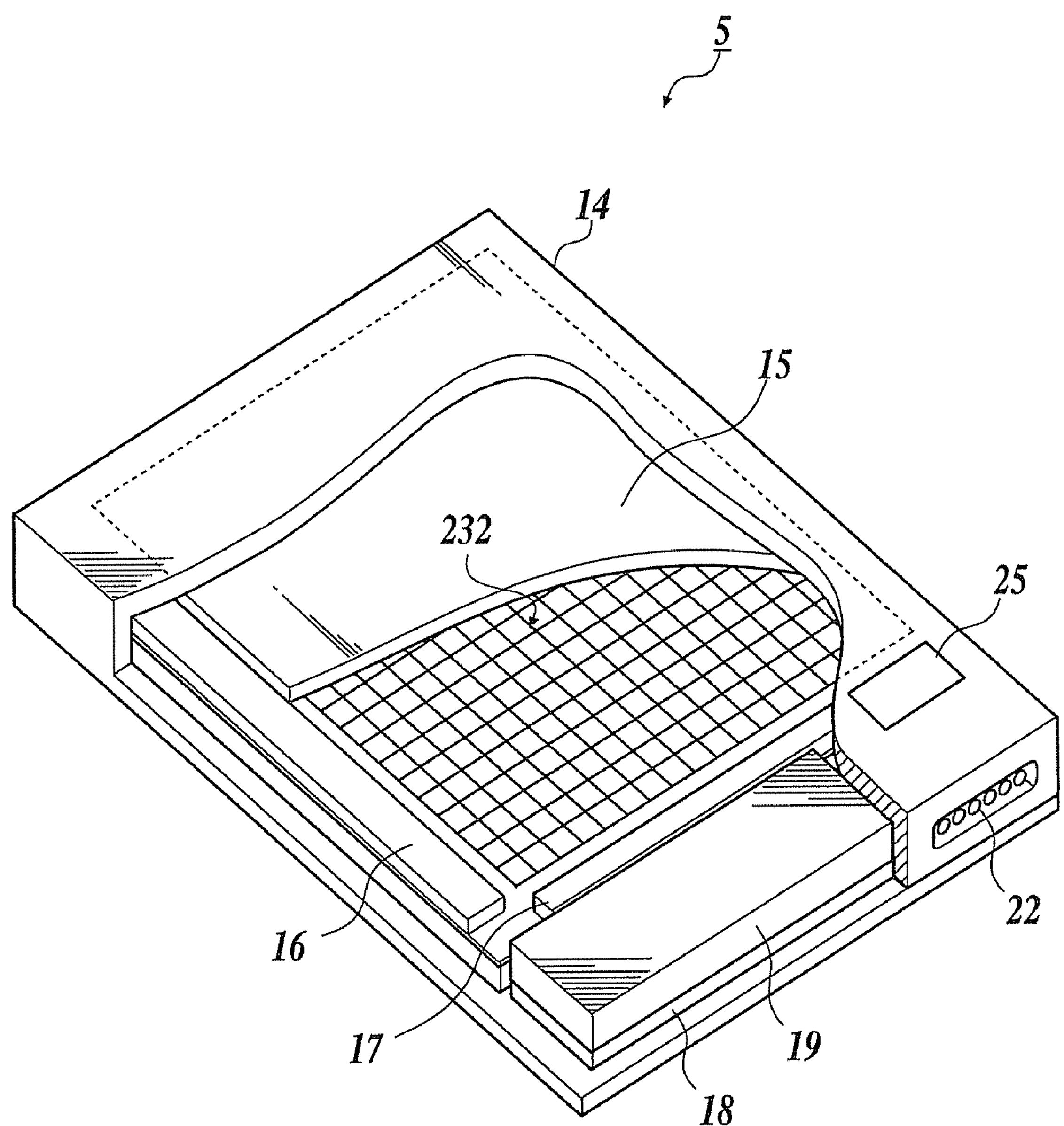
FIG. 3 is a perspective view showing the configuration of the principal part of a radiation image detector constituting the radiation image radiographing system of the FIG. 1.

The radiation image detector 5 is a radiation image detector that is a cassette type flat panel detector. As shown in FIG. 3, the radiation image detector 5 includes a housing 14 protecting the inner part, and is configured to be portable as a cassette.

In the inner part of the housing 14, image pickup panels 15 converting radiated radiations into an electric signal are formed in layers. On the radiation-irradiated surface sides of the image pickup panels 15, luminescent layers (not shown) emitting light according to the intensity of entered radiations are formed.

The luminescent layers are generally called as scintillator layers, and, for example, have a phosphor as their principal components. The luminescent layers output electromagnetic waves having the wavelengths in a range of from 300 nm to 800 nm, that is, the electromagnetic waves (lights) over ultraviolet lights to infrared lights around visible light rays on the basis of entered radiations.

For example, a phosphor containing $CaWO_4$ as a parent body, or a phosphor containing CsI:Tl, $Gd_2O_2S$:Tb, ZnS:Ag, or the like, as a parent body and a center material of light emission activated in the parent body can be used as the phosphor used for the luminescent layers. Moreover, a phosphor expressed by a general formula of $(Gd, M, Eu)_2O_3$ where M denotes a rare earth element can be used. In particular, CsI:Tl and $Gd_2O_2S$:Tb are preferable because they have a high radiation absorbed dose and luminous efficiency, and using these materials enables the obtainment of an image having low noises and high image quality.

On the surface opposite to the surface irradiated by the radiations of each of the luminescent layers, a signal detecting section 232 converting electromagnetic waves (lights) output from the luminescent layer into electric energy to accumulate the converted electric energy and outputting image signals based on the accumulated electric energy is formed.

Figure 4:
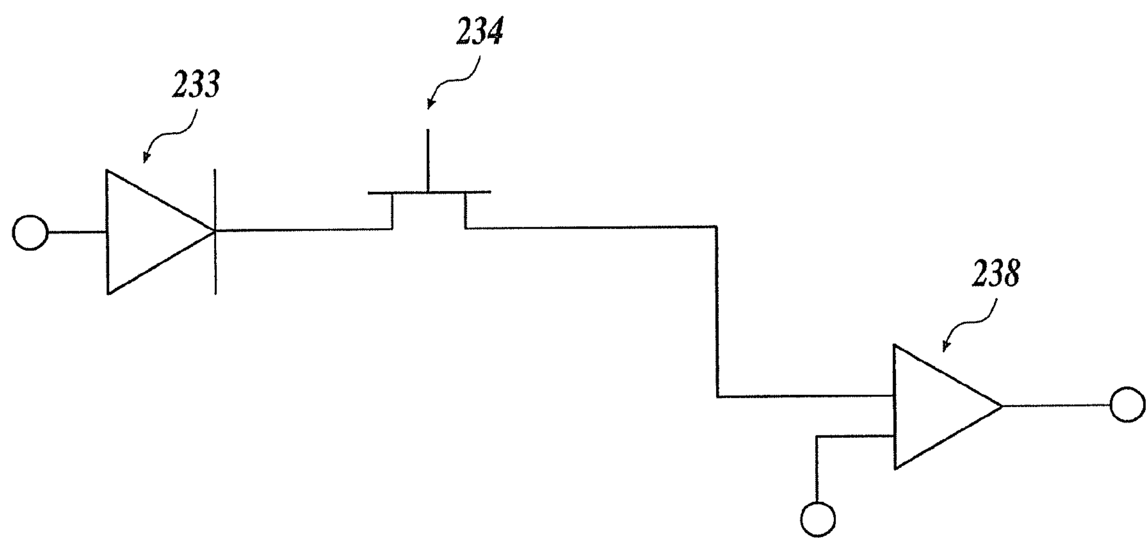
FIG. 4 is an equivalent circuit diagram of a photoelectric conversion section for one pixel constituting a photoelectric conversion layer included in the radiation image detector of the FIG. 3.

Now, the circuit configuration of the image pickup panel 15 is described. FIG. 4 is an equivalent circuit diagram of a photoelectric conversion section for one pixel constituting the signal detecting section 232.

As shown in FIG. 4, the configuration of the photoelectric conversion section for one pixel is composed of a photodiode 233 and a thin film transistor (hereinafter referred to as TFT 234) taking out the electric energy accumulated in the photodiode 233 by switching as an electric signal. The taken out electric signal is amplified by an amplifier 238 to a level that a signal reading circuit 17 can detect. Incidentally, a not-shown reset circuit composed of the TFT 234 and a capacitor is connected to the amplifier 238, and the amplifier 238 is configured so that a reset operation resetting accumulated electric signals is performed by switching the TFT 234. Incidentally, the photodiode 233 may be simply a photodiode having parasitic capacitance, or may be one including a parallelly connected additional capacitor in order to improve the dynamic range of the photodiode 233 and the photoelectric conversion section. Moreover, the photodiode 233 and the TFT 234 may be ones made of an inorganic semiconductor, which is used for a liquid crystal display and the like, or may be ones made of an organic semiconductor.

Figure 5:
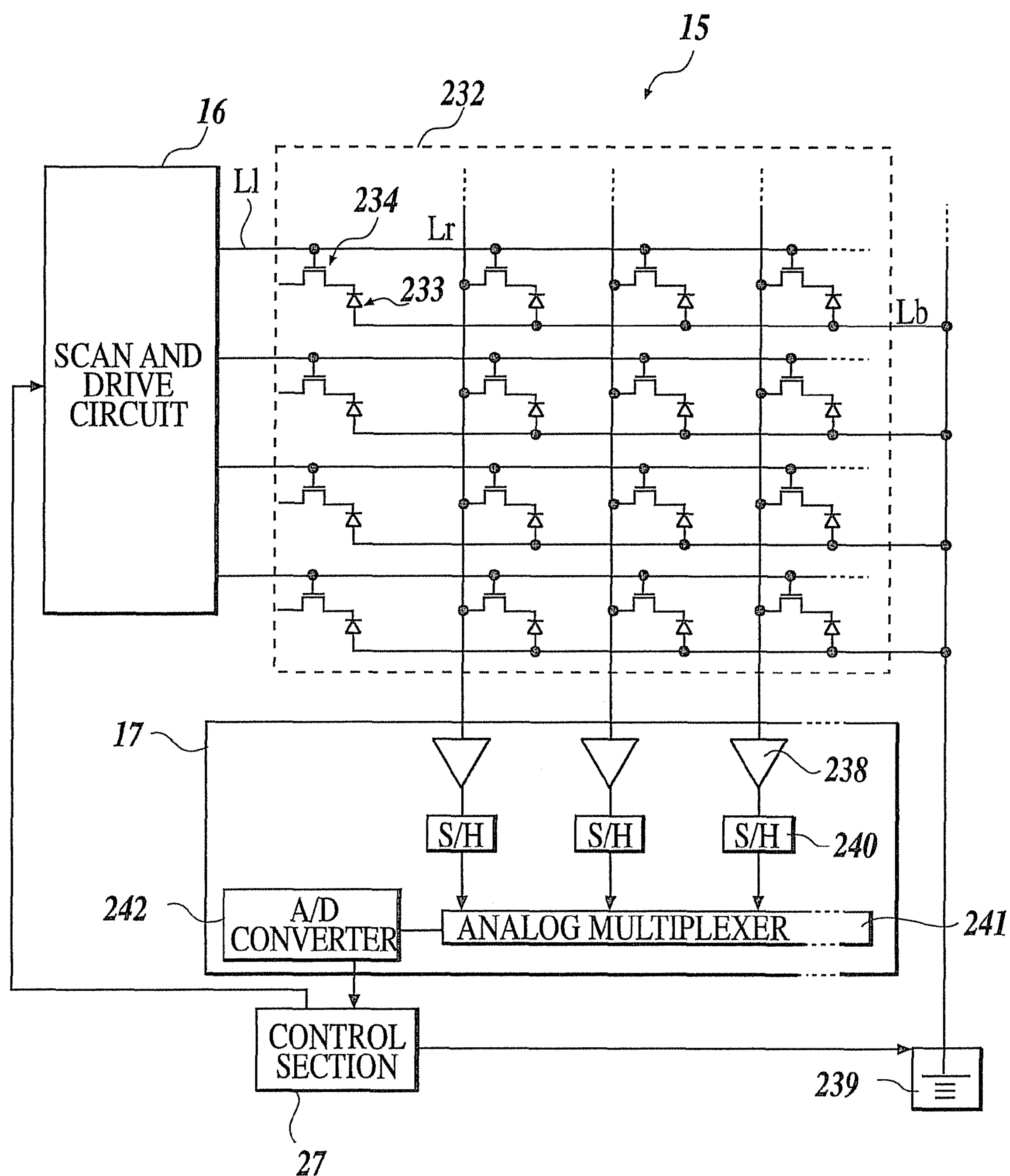
FIG. 5 is an equivalent circuit diagram of the two-dimensionally arranged photoelectric conversion section of the FIG. 4.

FIG. 5 is an equivalent circuit diagram including two-dimensionally arranged photoelectric conversion sections mentioned above, and scanning lines Ll and signal lines Lr are arranged between pixels so as to be perpendicular to one another. The TFTs 234 are connected to the aforesaid photodiodes 233, and one ends of the photodiodes 233 on the sides of the TFTs 234 are connected t the signal lines Lr. On the other hand, the other ends of the photodiodes 233 are connected to one ends of the adjoining photodiodes 233 arranged in each row, and are connected to a bias power source 239 through common bias lines Lb. One end of the bias power source 239 is connected to a control section 27, and the bias power source 239 is configured to apply a voltage to the photodiodes 233 through the bias lines Lb by an instruction from the control section 27. Moreover, the TFTs 234 arranged in each row are connected to common scanning lines Ll, and the scanning lines Ll are connected to the control section 27 through a scan and drive circuit 16. Similarly, the photodiodes 233 arranged in each column are connected to common signal lines Lr, and are connected to the signal reading circuit 17, which is controlled by the control section 27. The signal reading circuit 17 includes the amplifiers 238, sample hold circuits 240, an analog multiplexer 241, and an A/D converter 242, which are arranged on the common signal lines Lr in the order from the nearest one to an image pickup panel 23. Incidentally, although the case where the photodiodes 233 as photoelectric conversion elements are used have been described in the present embodiment, the photoelectric conversion elements may be solid state image pickup devices other than the photodiodes.

On the side portions of the signal detecting section 232, as shown in FIG. 3, the scan and drive circuit 16, which sends pulses to each photoelectric conversion element to scan and drive each photoelectric conversion element, and the signal reading circuit 17 reading the electric energy accumulated each photoelectric conversion element are disposed.

Figure 6:
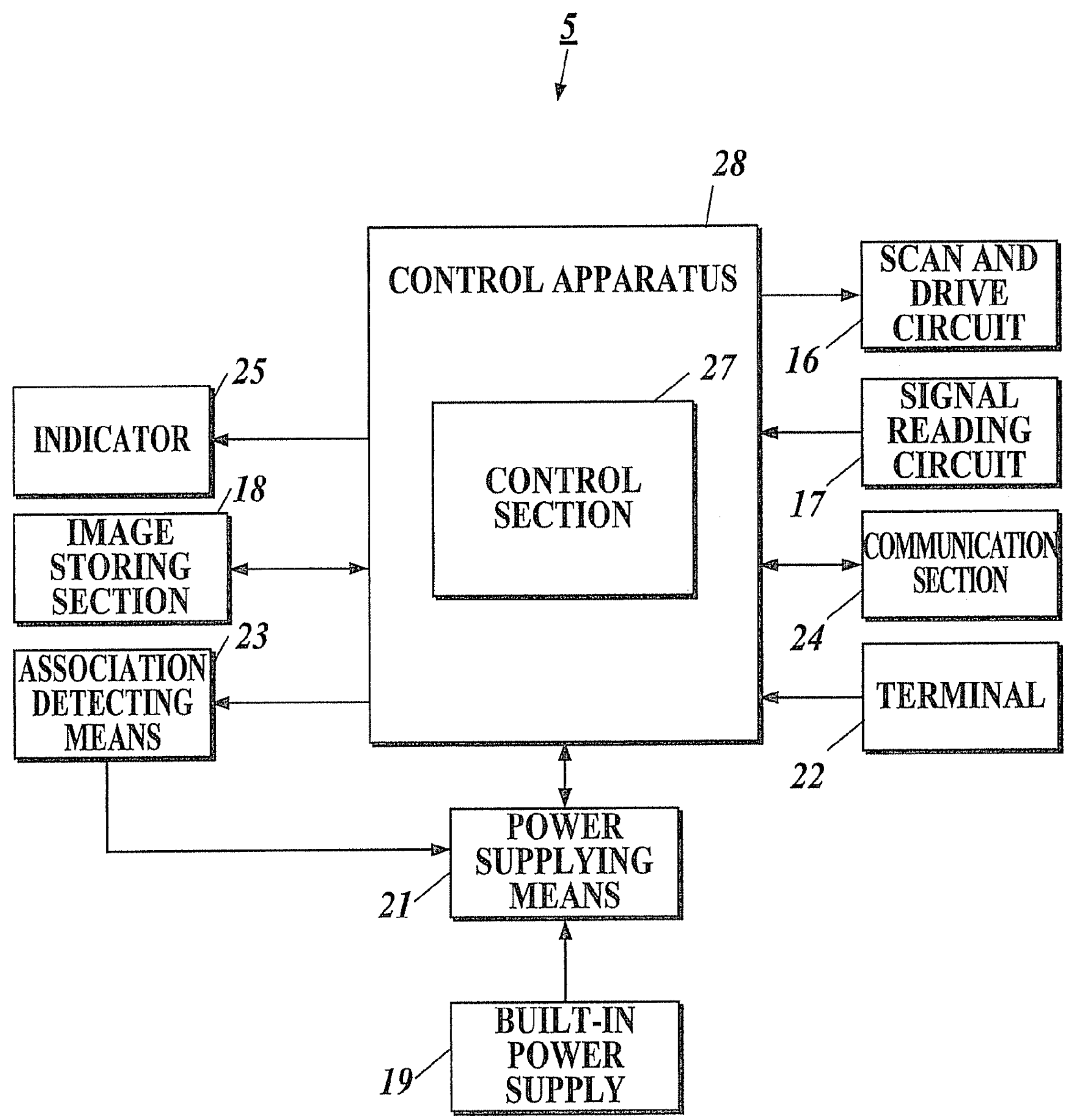
FIG. 6 is a block diagram showing the configuration of the principal part of the radiation image detector constituting the radiation image radiographing system of the FIG. 1.

Moreover, as shown in FIGS. 3 and 6, the radiation image detector 5 includes an image storing section 18 made of a rewritable memory, such as a flash memory and a RAM. The image storing section 18 stores image signals output from the image pickup panel 15, and may be either a built-in type memory or a detachably attachable memory such as a memory card.

Moreover, the radiation image detector 5 is provided with a built-in power supply 19 as a power supplying source supplying electric power to a plurality of drive sections (such as the scan and drive circuit 16, the signal reading circuit 17, the image storing section 18, the communication section 24 (to be described later), an indicator 25 (to be described later), and the image pickup panel 15) constituting the radiation image detector 5. As the built-in power supply 19, batteries such as a manganese battery, an alkaline battery, an alkaline button battery, a lithium battery, a silver oxide battery, a zinc-air battery, a mercury battery, and a lead-acid battery; rechargeable batteries capable of being recharged such as a nickel-cadmium battery, a nickel hydrogen battery, a lithium ion battery, a small-sized seal lead battery, and a lead storage battery; a fuel battery; a solar battery; and the like can be suitably selected to be composed. In the following description, a case of using a rechargeable battery is described.

A charging terminal 22 is formed at one end of the housing 14, and is configured so that the terminal (not shown) on the side of a charging apparatus 34, such as a cradle, and the terminal 22 on the side of the housing may be connected with each other to perform the charging of the rechargeable battery by, for example, fitting the radiation image detector 5 to the charging apparatus 34 as shown in FIG. 1. Moreover, the built-in power supply 19 is made to be exchangeable by, for example, being pulled out from the side portion of the housing 14.

Moreover, the radiation image detector 5 is provided with the communication section 24 (see FIG. 6) performing the transmission and the reception of various signals with an external apparatus, such as the consoles 6. The communication section 24 transfers, for example, an image signal output from the image pickup panel 15 and an operation state signal to the consoles 6, and receives radiography reserving instruction signals, radiography instruction signals, halt instruction signals, and the like, which are transmitted from the consoles 6 and the like.

Moreover, the housing 14 is configured to be provided with the indicator 25, which displays the charging situation of the built-in power supply 19, various operation situations, and the like, and informs of them, at one end on the surface of the housing 14 so that an operator can visually confirm the operation state of the radiation image detector 5, and the like.

Now, the radiation image detector 5 in the present embodiment is configured to be used in the state of being associated with a specific console 6 on the network 7. The association is performed by inputting the identification information (such as the ID and the bar code) of the radiation image detector 5 to be used for radiography from the input operating section 31 of the console 6 managing the radiographing room 11 to be used for the radiography in advance before performing the radiography at the time of installing the radiation image detector 5 into the radiographing room 11 to be used for the radiography. Moreover, another console 6 managing another radiographing room 11 may input the identification information of both of the console 6 managing the radiographing room 11 and the radiation image detector 5.

Incidentally, the input means of the association is not limited to the aforesaid example, but each apparatus having an input operating section on the network 7, a personal computer (PC), though it is not shown, which is installed in a diagnosis room where a doctor is present, or the like, may be used. Moreover, if the radiation image detector 5 includes an input operating section, the radiation image detector 5 may be used as the input means.

Moreover, the radiation image detector 5 is configured to grasp the console 6 associated with itself. As the means thereof, for example, it can be configured as follows. That is, when the association is performed, the information is sent to the server 2. Then, a couple of pieces of association information in the network 7 are generated and accumulated. Since then, each apparatus connected to the network 7 is only required to be configured to be able to share the association information accumulated in the server 2. Here, when association is performed, the association information is sent from the server to the radiation image detector 5 to which the association is performed. Alternatively, by performing the periodical access to the association information in the server 2 through the communication section 24, the radiation image detector 5 grasps which is the console 6 on the network 7 that is associated with itself.

Incidentally, also the method of grasping the association is not limited to the aforesaid example, but also the following method may be adopted. That is, once the association has been performed, the control section 29 that has performed the association transmits the information to the server and the associated radiation image detector 5, the control section 27 of the radiation image detector received the information grasps the console 6 in relation with being associated with itself. Only the required thing to the association is to be able to determine the combination of the console 6 and the radiation image detector 5 on the network 7, and the method of determining the combination, the order, the means, the timing, and the like, at that time do not matter.

Moreover, the radiation image detector 5 updates the associated console 6 by overwriting it every performance of association. That is, the radiation image detector 5 is configured to releases the association with the previously associated console 6, and to grasp the association with the console 6 having the newly input identification information. Incidentally, it is preferable to configure the radiation image detector 5 so that, once the radiography instruction signal is input, it becomes impossible to release the association with the associated console 6 until a predetermined time has elapsed.

Moreover, the radiation image detector 5 includes an association detecting means 23 for detecting the operation status of the console 6 associated with itself. The association detecting means 23 is configured to transmit a confirmation signal for confirming the operation status of the console 6 to the console 6 associated with itself when association is performed, and to detect the operation status of the console 6 associated with itself on the basis of a signal (operation status signal) indicating the in-operation of the console 6, which is sent from the console 6 to the confirmation signal.

Incidentally, as the method by which the association detecting means 23 detects the operation status of the console 6 associated with itself is not limited to the example mentioned above, but the method may be configured to detect the operation state on the basis of the transmission of an operation status signal from the control section 29 of the console 6 to the radiation image detector 5 associated with the console 6 when an association instruction is input into the console 6.

Moreover, the timing when the association detecting means 23 detects the operation status of the console 6 associated with itself is not limited to the aforesaid example, but the detection may be performed at the reception of a start-up instruction input with the input operating section 31 of the console 6 or the reception of various instruction signals transmitted on the basis of various instructions such as a radiography reserving instruction. Furthermore, the association detecting means 23 may periodically transmit a confirmation signal to the console 6 associated with itself during the radiation image detector 5 in operation. In this case, if the radiation image detector 5 does not receive any reply signals, then it is possible to detect that the console 6 associated with the radiation image detector 5 has not been started, or that the console 6 associated with itself has broken and the console 6 is in the unusable state for radiography.

Moreover, the radiation image detector 5 is provided with power supplying means 21 for controlling the state of the electric power to be supplied from the built-in power supply 19 to each drive section of the radiation image detector 5 according to the operation status of the console associated with itself which console has been detected by the association detecting means 23. The radiation image detector 5 includes the state of being capable of radiography, the state of waiting radiography, and the state of preparing waiting as a plurality of states of power supply different in power consumption quantities, and the radiation image detector 5 is configured to be able to switch and set the states of power supply by the power supplying means 21.

In the following, the state of being capable of radiography, the state of waiting radiography, and the state of preparing waiting are described.

In the state of being capable of radiography, a radiography operation is performed, and the state of being capable of radiography is the state in which electric power is supplied to the drive sections necessary for the radiography operation. The state of being capable of radiography is the state in which electric power is supplied to at least the drive sections necessary for detecting a radiation. In the present embodiment, electric power is supplied to the drive sections, such as the scan and drive circuit 16, the signal reading circuit 17, the photodiodes 233, the TFTs 234, the image storing section 18, and the communication section 24, and it becomes possible to perform a series of radiography operations of each operation of the initialization of the image pickup panel 15, the accumulation of the electric energy generated according to radiated radiations, the reading of electric signals, the transfer of image signals, and the like. Incidentally, in initialization, it is set to perform a reset operation and an empty reading operation in the image pickup panel 15.

On the other hand, in the state of waiting radiography, no radiography operations are performed, but the state is that of consuming electric power less than that of the state of being capable of radiography, and that of supplying electric power to each of the drive sections to enable quick shifting to the state of being capable of radiography. The state of waiting radiography can be configured to supply electric power, for example, to the drive sections except the signal reading circuit 17 capable of quick shifting to the state of being capable of radiography. In the present embodiment, the electric power is supplied to the drive sections such as the scan and drive circuit 16, the photodiodes 233, the TFTs 234, the image storing section 18, the communication section 24, and the indicator 25. That is, the state of waiting radiography is the state capable of dealing with the situation in which there is no possibility of immediately starting a radiography operation but there is the possibility of performing a radiography operation while reducing the useless power consumption at the time of not radiographing.

Moreover, also the state of preparing waiting is the state of not performing any radiography operations, but the state of preparing waiting is that of consuming less electric power than that of the state of waiting radiography, and is the one capable of starting on the basis of a signal from the console 6. The state of preparing waiting is the one capable of at least receiving a signal from the console 6 to make the operation state of the radiation image detector 5 transit. In the present embodiment, for example, electric power is supplied to the communication section 24. That is, the state of preparing waiting cannot deal with the situation in which there is the possibility of performing a radiography operation, but is the state capable of considerably reducing the useless power consumption at a non-radiographing time.

The radiation image detector 5 having such a state of power supply is configured to set the operation state thereof in the state of waiting radiography with the power supplying means 21 when the association detecting means 23 detects the operation of the console 6 associated with the radiation image detector 5, for example, when the association detecting means 23 detects that a start-up instruction signal has input into the control section 27 through the communication section 24.

Furthermore, the radiation image detector 5 is configured to set the operation state thereof in the state of being capable of radiography with the power supplying means 21 when the association detecting means 23 detects that the console 6 associated with the radiation image detector 5 has started to start radiography operations, for example, when the association detecting means 23 detects that a radiography reserving instruction has been input into the console 6 and that the radiography reserving instruction signal has been input into the control section 27 through the communication section 24.

Moreover, the radiation image detector 5 is configured to set the operation state thereof in the state of preparing waiting with the power supplying means 21 when the association detecting means 23 detects that the console 6 associated with the radiation image detector 5 has not started yet, for example, when the association detecting means detects that a halt instruction signal has input into the control section 27 through the communication section 24.

Moreover, the radiation image detector 5 is configured to set the operation state thereof in the state of waiting radiography after a predetermined time has elapsed when the association detecting means 23 detects that no radiography instruction signals have been input into the control section 27 during a predetermined time after the operation state has been set in the state of being capable of radiography. Moreover, the power supplying means 21 is configured to set the operation state of the radiation image detector 5 in the state of waiting radiography after the end of a radiography operation.

The power supplying means 21 can hereby change its own operation state by changing the power supplying state of the radiation image detector 5 according to the operation status of the console 6 associated with the radiation image detector 5.

Moreover, as shown in FIG. 6, the radiation image detector 5 includes a control apparatus 28 having the control section 27 composed of, for example, a general purpose a CPU, a ROM, a RAM, and the like (all of which are not shown). The control section 27 is configured to read a predetermined program stored in the ROM, to expand the read program in the working area of the RAM, and to execute various kinds of processing in accordance with the program with the CPU.

The radiation image detector 5 is configured so that a signal received by the communication section 24 is input into the control section 27, and the control section 27 is configured to perform the control of each drive section on the basis of the signal received by the communication section 24. For example, when the communication section 24 has received a radiography instruction signal, a radiography reserving instruction signal, and a halt instruction signal, the control section 27 makes the power supplying means 21 change the operation state of the radiation image detector 5 mentioned above on the basis of the received instruction signals.

Moreover, the control section 27 outputs the operation state information indicating which state among the operation states the radiation image detector 5 is in operation as the operation state of the radiation image detector 5, and transmits the output operation state information to the associated console 6 through the communication section 24 as an operation state signal.

Moreover, the control section 27 drives the scan and drive circuit 16 to transmit a pulse to each photoelectric conversion element, and thereby scans and drives each of the photoelectric conversion elements. The control section 27 then makes the signal reading circuit 17 read the electric energy accumulated in each photoelectric conversion element, and makes the signal reading circuit 17 send the read image signal to the control section 27. The control section 27 makes the image storing section 18 store the sent image signal, and makes the communication section 33 send the image signal to the console 6 through the communication section 24.

Next, the operation of the radiation image radiographing system 1 according to the present embodiment is described.

When a radiation image detector 5 is newly installed in a radiographing room 11 to use the radiation image detector 5 for radiography, a console 6 registers the radiation image detector 5 to be used for radiography in advance, and associates the radiation image detector 5 with the console 6.

To put it concretely, when the radiation image detector 5 is installed in the radiographing room 11 to be used for radiography, a radiological technician inputs the identification information of the radiation image detector 5 to be installed with the input operating section 31 of the console 6 in operation managing the radiographing room 11. Then, the control section 29 associates the console 6 with the radiation image detector 5, and simultaneously transmits association information to the server 2 through the communication section.

The radiation image detector 5 thereupon grasps the console 6 associated with itself on the basis of the association information sent from the server 2.

The control section 29 then transmits a confirmation signal to the console 6 associated with itself through the communication section 24.

The control section 29 of the console received the confirmation signal transmits an operation status signal through the communication section 33 as the information indicating its own operation status.

After that, the control section 27 of the radiation image detector 5 received the operation status signal makes the association detecting means 23 detect the operation status of the console 6 associated with itself. If the association detecting means 23 detects that the console associated with the control section 27 has started, then the control section 27 makes the power supplying means 21 change the operation state of the radiation image detector into the state of waiting radiography change. On the other hand, if the association detecting means 23 detects that the console associated with the control section 27 has not started, then the control section 27 makes the power supplying means 21 change the operation state of the radiation image detector into the state of preparing waiting change.

The radiation image detector 5 used in the radiographing room 11 and the console 6 managing the radiographing room 11 have been put in the state of being mutually associated in this way, and a patient to be radiographed next and a radiation image detector 5 to be used for the patient are selected in a radiography list at the time of performing radiography. Then, the radiography is performed.

To put it concretely, a radiological technician inputs a start-up instruction with the input operating section 31 of the console 6 in the state of being associated with the radiation image detector 5, and the control section 29 starts up the console 6 and transmits a start-up instruction signal through the communication section 33 to the associated radiation image detector 5.

When the radiation image detector 5 receives the start-up instruction signal, the radiation image detector 5 detects with the association detecting means 23 that the console 6 associated with itself has started, and the power supplying means 21 controls the state of power supply of the electric power supplied from the built-in power supply 19 to each drive section of the radiation image detector 5 to change the operation state of the radiation image detector 5 to the state of waiting radiography.

Then, when a radiological technician selects a patient to be radiographed next and a specific radiation image detector 5 to be used for the patient in the radiography list transmitted from the server 2 or the like with the input operating section 31 of the console 6 managing the radiographing room 11 at the time of radiography, the identification information of the radiation image detector 5 to be used for the radiography performed next in the radiographing room 11 is input, and the radiography reserving instruction is input into the input operating section 31.

When the radiography reserving instruction is input, the control section 29 selects the association with the radiation image detector 5 the identification information of which has been input among the associated radiation image detectors 5, and simultaneously transmits the radiography reserving instruction signal to the communication section 24 of the radiation image detector 5 the association with which has been selected by the input of the identification information through the communication section 33.

After that, the radiation image detector 5 receives the radiography reserving instruction signal through the communication section 24, and the information thereof is output to the control section 27.

When the control section receives the radiography reserving instruction signal, the control section 27 makes the power supplying means 21 changes the operation state of the radiation image detector into the state of being capable of radiography, and simultaneously transmits an operation state signal to the console 6 associated with itself through the communication section 24. The control section 29 of the console 6, which has received the operation state signal, makes the display section 32 display the operation state of the radiation image detector 5. Since then, the radiation image detector 5 suitably transmits an operation state signal of the radiation image detector 5 to the console 6 associated with itself, and the associated console 6 associated with the radiation image detector 5 makes the display section 32 display the operation state of the radiation image detector 5.

During a predetermined time from the change to the state of being capable of radiography, the radiation image detector 5 then detects whether radiography instruction information is input into the control section 27.

During this period, the radiography instruction is input from the input operating section 31 of the console 6, and the radiography instruction information is transmitted to the radiation radiating operation apparatus 3 and the radiation image detector 5 through the communication section 33.

After that, the radiation radiating operation apparatus 3 receives the radiography instruction information, and controls the radiation radiating apparatus 10 to radiate radiations from the radiation source 12. The image pickup panel 15 of the radiation image detector 5 thereupon detects the radiations, and converts the detected radiations into electric signals to accumulate them. After that, the control section 27 makes the scan and drive circuit 16 scan and drive, and makes the signal reading circuit 17 read the electric energy accumulated in each photoelectric conversion element to make the image storing section 18 store the read image signal and to transmit the read image signal to the communication section 33 of the associated console 6 through the communication section 24.

Here, if no radiography instruction information is input into the control section 27 during the predetermined time from the change to the state of being capable of radiography, then the power supplying means 21 changes the operation state of the radiation image detector to the state of waiting radiography after the elapse of the predetermined time, and stands by until a radiography reserving instruction signal is again received by the communication section 24.

Then, the radiography operations ends, and the power supplying means 21 of the radiation image detector 5 changes the operation state to the state of waiting radiography. The radiation image detector 5 stands by until a radiography reserving instruction signal is again received by the communication section 24.

After that, when the console 6 receives an image signal from the radiation image detector 5 through the communication section 33, the control section 29 performs image processing, and then makes the display section 32 display the processed image signal as the radiation image information detected by the radiation image detector 5.

Incidentally, when an instruction instructing the stop of the operation of the console is input from the input operating section 31 of the console 6 by a radiological technician in the operation since the radiation image detector 5 has been associated with the console 6 on the network 7, an operation stop instruction is input into the control section 29, and the control section 29 transmits the operation stop instruction signal to the radiation image detector 5 associated with the console 6 through the communication section 33. After that, the control section 29 turns off the power source of the console 6. On the other hand, when the operation stop instruction signal is input into the control section 27 of the radiation image detector 5 through the communication section 24, the electric power control section 21 detects the instruction, and sets the operation state of the radiation image detector 5 in the state of preparing waiting. Then, the radiation image detector 5 stands by until a start-up instruction signal is received by the communication section 24.

After that, when the radiological technician inputs an instruction of starting the console with the input operating section 31 of the console 6, a start-up instruction is input into the control section 29, and the start-up instruction signal is transmitted to the radiation image detector 5, which has been already associated, through the communication section 33. When the start-up instruction signal is input into the radiation image detector 5 though the communication section 24, the electric power control section 21 detects that effect to set the operation state of the radiation image detector 5 in the state of waiting radiography, and the radiation image detector 5 stands by until the communication section 24 receives a radiography reserving instruction signal がreceive.

Incidentally, if the radiation image detector 5 has moved to another radiographing room 11 after that, the identification information of the radiation image detector 5 is input from the input operating section 31 of the console 6 managing the radiographing room 11 by a radiological technician, for example, at the time of being carried into the radiographing room 11 of the moving destination. At this time, if the console 6 managing the radiographing room 11 of the moving destination does not started yet, then a start-up instruction is input from the input operating section 31 of the console 6 after the console 6 has been started, and the identification information of the radiation image detector 5 is input.

When the identification information has been input, the control section 29 performs the association with the radiation image detector 5 to which the identification information has been input, and simultaneously releases the association with the radiation image detector that has been previously associated. The control section 29 then transmits the association information pertaining to the newly performed association to the server 2.

Thereupon, the association information is sent from the server 2 to the newly associated radiation image detector 5.

The radiation image detector 5 received the association information grasps the console 6 associated with itself on the basis of the association information sent from the server 2.

When the next radiography is performed in the radiographing room of the moving destination, the console 6 managing the radiographing room operates the radiation image detector 5 at the time of radiography, and the image signals read by the radiation image detector 5 are transmitted to the newly associated console 6.

As described above, according to the present embodiment, the radiation image detector 5 is associated with a specific console 6 on the network 7, and the association detecting means 23 detects the operation status of the associated console 6. The radiation image detector 5 can automatically change it own state of power supply, namely, the operation state thereof, according to the operation status.

At that time, if the associated console 6 has started and a radiography reserving instruction has been input, then the radiation image detector 5 starts in the state of being capable of radiography, and a radiography operation is performed in the state when a radiography instruction is input.

On the other hand, when no radiography instructions are input from the console 6 for a predetermined time from the state of being capable of radiography has been set even if the associated console 6 has started and the radiography reserving instruction has been input, for example, when the radiography is wanted to be interrupted owing to some accident, the radiation image detector 5 sets the operation state thereof in the state of waiting radiography, and can quickly shifts the operation state thereof to the state of being capable of radiography while reducing useless power consumption.

Moreover, if the associated console 6 has started and no radiography reserving instructions have been input, for example, in the situation in which there is no possibility of immediately starting a radiography operation but it is expected to perform a radiography operation, such as daytime radiography in a hospital, the radiation image detector 5 sets the operation state thereof in the state of waiting radiography, and can quickly shifts the operation state into the state of being capable of radiography while reducing useless power consumption.

Moreover, if the associated console 6 has not started, for example, in the case where it is expected that almost no radiography operations are performed, such as the case of night radiography in a hospital, then the radiation image detector 5 has been started by setting the operation state thereof in the state of preparing waiting, and in the state capable of transiting the state thereof at any time by receiving an external signal with the communication section 24. Consequently, useless power consumption can be considerably reduced, and it is also possible to prevent forgetting to turn off the power source of the radiation image detector 5.

Consequently, the radiation image radiographing system 1 can remove the trouble of the operation for starting the radiation image detector 5 and the time for waiting for the start-up thereof, and the operationality at the time of radiography can be improved. Moreover, it can be prevented that a patient is obliged to be re-radiographed by using the radiation image detector 5 that is not started by mistake owing to forgetting turn on the power source of the radiation image detector 5, and it is also prevented that a patient is subjected to unnecessary exposure owing to an error in operation.

Moreover, even if the radiation image detector 5 is moved to be installed in another radiographing room 11 and the radiation image detector 5 is used in the radiographing room 11, an image signal can be transmitted to the associated console 6, and consequently the flexibility of the configuration of the network 7 can be improved to further improve the operationality thereof at the time of radiography.

Moreover, because the console 6 can make the display section 32 display the operation state thereof among the various kinds of information of the radiation image detector 5 that has been associated during the operation thereof, a radiological technician can confirm the associated operation state of the radiation image detector 5 on the console 6, and can perform the processing such as giving the next instruction according to the operation state. Consequently, the operationality at radiography can be improved.

Incidentally, it is needless to say that the present invention is not limited to the above embodiment, and that the present invention can be suitably changed.

In the present embodiment, although the operation state of the radiation image detector 5 includes three kinds of states (the state of being capable of radiography, the state of waiting radiography, and the state of preparing waiting), the operation state is not limited to the illustrated three kinds. For example, the power supplying states may be the following states: the state of waiting radiography in which only the power supply to the photodiodes 233 and the TFTs 234, which have the characteristic of deteriorating with time, is stopped; and the state of waiting radiography, in which the whole power supply to the sections other than the image storing section 18 and the communication section 24 is stopped, but in which the supply of electric power is started earlier only to the photodiodes 233 and the TFTs 234, the power supply to which takes a longer time after the power supply has been once stopped until the power supply is again started up, than to the other drive sections. Furthermore, the power supplying states may also include a plurality of kinds of the states of waiting radiography.

Moreover, although the communications with various apparatus on the network 7 are performed by the wireless communication system in the present embodiment, the communications may be performed by a wired communication system. In this case, the radiation image detector 5 is not required to start the communication section 24 and to always detect the signals from the console 6. It is possible to start the radiation image detector 5 when a signal sent from an apparatus on the network 7 through a cable or the like is input to the radiation image detector radiation image detector 5. Consequently, it is possible to set the state of preparing waiting, in which power consumption is the least among the operation states of the radiation image detector 5, in the state in which no electric power is supplied to the radiation image detector 5 at all to enable to perform the turning on/off of the power source of the radiation image detector 5 correspondingly to the turning on/off of the power source of the console 6.

For example, although an instruction of radiography reservation is input by the selection of the radiation image detector 5 to be used for the radiography to a patient scheduled to be radiographed in the present embodiment, there may be adopted the configuration of inputting a radiography reserving instruction by selecting a patient on a radiography list if the patients to whom radiation image detectors scheduled to be used have been determined in advance are listed in the radiography list.

Moreover, it is also possible that the console 6 detects the cognitive information of a radiation image detector 5 having an attached integrated circuit (IC) tag through a sensor at the time of bringing the radiation image detector 5 into a radiographing room by passing the radiation image detector 5 though the sensor provided at the entrance and exit of the radiographing room without manual input with the console 6 and the radiation image detector 5.

Moreover, the base station 4 can also function as the sensor. In this case, a base station 4 is provided at each certain area in the network 7, and each base station 4 can recognize the radiation image detectors 5 existing in the scope that each base station 4 manages to associate the radiation image detectors to the console associated to each base station 4.

Moreover, although the present embodiment separates an association action of associating a console 6 with a radiation image detector 5 and a radiography action as a trigger of performing a radiography operation (input action of an radiography reserving instruction in the console 6) and both the actions are not performed at the same time, both the actions may be commonly performed, and the association action and the radiography action may be simultaneously performed.

In this case, when the radiation image detector 5 is installed in the radiographing room to be used for radiography, a radiological technician inputs the identification information of the radiation image detector 5 to be installed with the input operating section 31 of the console 6, and simultaneously accesses the server 2 and selects patient to be radiographed next in a radiography list to input the patient. In the input operating section 31 of the console 6, the console 6 with which the identification information has been input, the radiation image detector 5 the identification information of which has been input, and the patient to be radiographed nest with the radiation image detector 5 are thereupon mutually associated, and the inputs of an association instruction and a radiography reserving instruction are simultaneously performed. The input operating section transmits the association information to the server 2 through the communication section 33, and at the same time transmits an operation status ignal to the associated radiation image detector 5.

Next, in the radiation image detector 5, the control section 27 simultaneously performs the grasp of the console 6 associated with itself on the basis of the association information sent from the server 2 and the detection of operation status of the console 6 associated with itself with the association detecting means 23.

When the association detecting means 23 detects that the console associated with itself has started, the control section 27 makes the power supplying means 21 change the operation state of the radiation image detector to the state of being capable of radiography, and since then the continuing radiography operations are performed.

The radiation image radiographing system 1 configured to simultaneously input the instructions of association and radiography reservation in this manner omits the trouble of the operation for starting the radiation image detector 5 and the time of waiting for start-up in the case where radiography is wanted to be performed especially urgently (for example, in the case of the association is performed with the started console).

Second Embodiment

Next, a second embodiment is described.

The radiation image radiographing system 1 of the first embodiment controls the power supplying state according to the operation status of a console as an example of the state of the console associated with a radiation image detector, that is, the radiation image radiographing system 1 detects the operation status of the associated console to control the power supplying state of the radiation image detector according to the detected state. On the other hand, in the second embodiment, a description is given to the case where the power supplying state is controlled according to the stages of progress of the operation performed in the associated console. Accordingly, in the following description, the descriptions of the control sections of the radiation image detector 5 and the console 6 are performed with priority, and the descriptions of the portions similar to those in the first embodiment are omitted, and the same marks are attached to those portions to be described.

The console 6 is first described.

Figure 7:
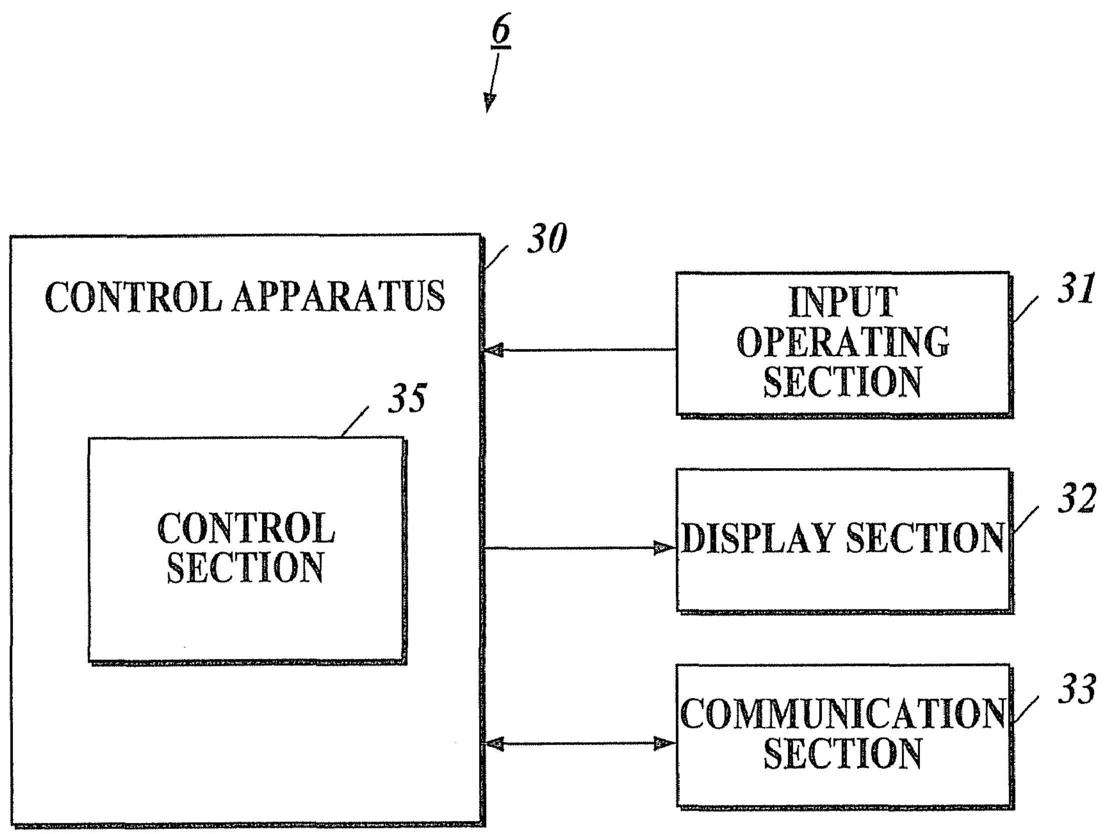
FIG. 7 is a block diagram showing the configuration of the principal part of a console in a second embodiment of the radiation image radiographing system according to the present invention.

As shown in FIG. 7, the console 6 includes the input operating section 31, the display section 32, the communication section 33, and the like, and each member is connected to a control section 35 in the control apparatus 30. Incidentally, an identification number (such as an ID and a bar code) for distinguishing the plurality of consoles 6 on the network 7 is given to each console 6.

In the present embodiment, the input operating section 31 is configured to input, for example, an association instruction, a radiography reserving instruction, and a radiography instruction as input instructions.

The control section 35 is configured to receive an input instruction from the input operating section 31 and information received from the outside through the communication section 33, and performs the predetermined processing of input instruction or information.

For example, when an association instruction is input with the input operating section 31, the control section 35 performs the association of the radiation image detector 5 the identification information of which has been input with the input operating section 31 with the console 6, and transmits an association changing signal to the communication section 24 of the radiation image detector 5 associated with the console 6 through the communication section 33.

Incidentally, when only the identification information of the radiation image detector 5 to be used in the radiographing room 11 has been input with the input operating section 31, the control section 35 performs the association of the radiation image detector 5 having the input identification information with the console 6.

Moreover, when an association instruction is input with the input operating section 31, the control section 35 adds the radiation image detector 5 to be associated at each time it occurs.

Moreover, when a radiography reserving instruction is input with the input operating section 31, the control section 35 selects the radiation image detector 5 selected with the input operating section 31 among the radiation image detectors 5 that have been already associated with itself. That is, the radiography reserving instruction associates a patient to be radiographed with the radiation image detector 5 to be used for the patient by selecting the radiation image detector 5 to be used for the patient among the radiation image detectors 5 that have been already associated to the patient to be radiographed.

Moreover, when a certain radiation image detector 5 is selected on the basis of the input of a radiography reserving instruction, the control section 35 transmits a radiography reserving instruction signal to the communication section 24 of the radiation image detector 5 having the selected identification information through the communication section 33.

Moreover, when a radiography instruction is input with the input operating section 31, the control section 35 transmits a radiography instruction signal to the communication section 24 of the radiation image detector 5 through the communication section 33.

Moreover, when radiation image information detected by the radiation image detector 5 is input through the communication section 33, the control section 35 performs predetermined image processing.

Moreover, the control section 35 is configured to make the display section 32 display instructions, information, or the like, input with the input operating section 31 and the communication section 33, and makes the display section 32 display a radiation image, a thumbnail image, the operation information of the radiation image detector 5 associated with the console 6, and the like, besides the aforesaid radiography list and the like. As the operation information of the radiation image detector 5 associated with the console 6, there can be cited, for example, the information of the releasing of the association with the console 6 and the information of the operation of the associated radiation image detector 5.

Next, the radiation image detector 5 is described.

Figure 8:
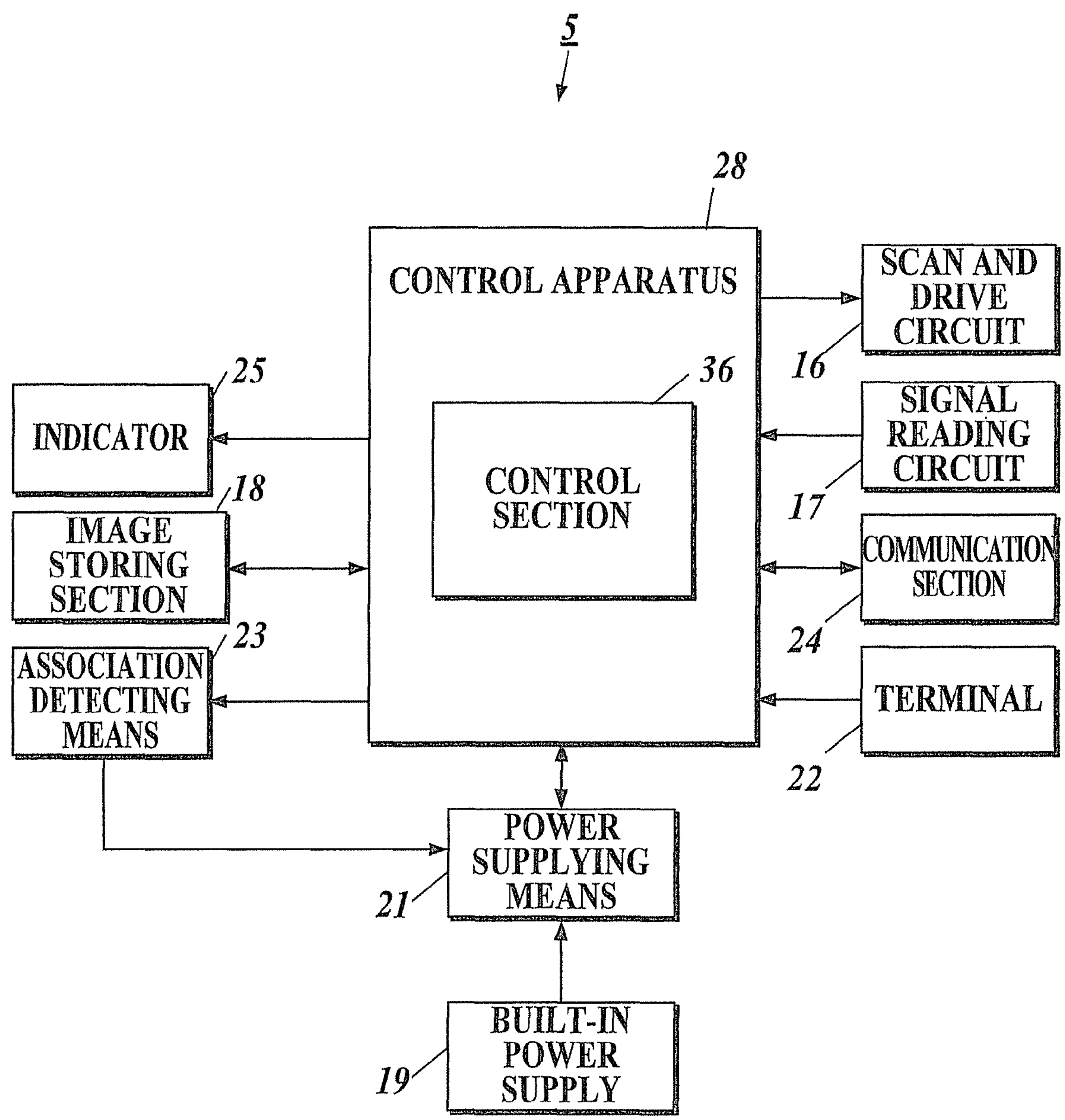
FIG. 8 is a block diagram showing the configuration of the principal part of a radiation image detector in the second embodiment of the radiation image radiographing system according to the present invention.

As shown in FIG. 8, the radiation image detector 5 is provided with the image pickup panel 15, the scan and drive circuit 16, the signal reading circuit 17, the image storing section 18, the communication section 24, the indicator 25, and the built-in power supply 19. As shown in FIG. 8, each of these members is connected to a control section 36 in the control apparatus 28. Incidentally, each radiation image detector 5 is given an identification number (such as an ID and a bar code) for distinguishing the plurality of radiation image detectors 5 on the network 7.

Incidentally, the communication section 24 in the present embodiment transfers, for example, an image signal output from the image pickup panel 15 to the console 6, and receives an association changing instruction signal, a radiography instruction signal, and the like, transmitted from the console 6 or the like.

Moreover, the radiation image detector 5 is provided with detecting means 40 for confirming the progress of the operation based on an instruction from the console associated with itself.

The detecting means 40 is configured to detect whether the operation based on an instruction from the console 6 associated with the radiation image detector 5 has been completed, and to output that effect to the control section 36 on the basis of an instruction from the control section 36, to which the association changing signal has been input. Moreover, the detecting means 40 is configured so that, when the detecting mean 40 detects that the operation based on the instruction from the console 6 associated with the radiation image detector 5 has been completed, the detecting means 40 outputs that effect to the control section 36.

As an operation performed by the radiation image detector 5, there are a radiography operation in the state of being capable of radiography and a radiography waiting operation in the state of waiting radiography or the state of preparing waiting, and these operations can be changed and set by the control section 36.

Moreover, the radiation image detector 5 is provided with releasing means 41 for releasing the association with the associated console 6 on the basis of an instruction from the control section 36.

The radiation image detector 5 is configured so that a signal received by the communication section 24 is input into the control section 36, and the control section 36 is configured to perform the control of each drive section on the basis of the signal received by the communication section 24. For example, the control section 36 is configured so that, when the communication section 24 has received an association changing instruction signal including the identification information of the control section 36, the control section 36 makes the detecting means 40 perform an operation of confirming the transmission situation of image data as the progress of the operation based on an instruction from the console 6 associated with the control section 36.

Moreover, the control section 36 is configured so that, when the control section 36 receives an input of a signal indicating the completion of the operation of the console 6 associated with itself, for example, a signal indicating that image data has been transmitted, from the detecting means 40, the control section 36 makes the releasing means 41 release the association with the console 6 associated with itself, and that the control section 36 transmits a signal indicating the release of the association to the communication section 33 of the console 6 the association with which is to be released through the communication section 24. Incidentally, the control section 36 of the radiation image detector 5 the association of which with a specific console 6 has been released is configured to control to make is possible to be associated with a new console 6. The control section 36 is configured so that, after the control section 36 has transmitted the signal indicating the release of the association, the control section 36 performs the association with the console (the next console 6) to which the association changing instruction signal including the identification information of the control section 36 has been transmitted.

On the other hand, the control section 36 is configured so that, when a signal indicating that the operation of the console 6 associated with itself has not been completed, for example, a signal indicating that image data has not been transmitted yet, is input from the detecting means 40, the control section 36 makes the releasing means 41 not release the association with the console 6 associated with itself, and transmits a signal indicating the imperfectness of the operation to the console 6 (the next console 6) to which the control section has transmitted the association changing instruction signal including its own identification information through the communication section 24. The control section 36 is configured so that, after the control section 36 has transmitted the signal indicating the imperfectness of the operation, the control section makes each drive section perform the continuing operation.

Moreover, the control section 36 is configured so that, when a radiography instruction signal is input through the communication section 24, the control section 36 drives the scan and drive circuit 16 to transmit a pulse to each photoelectric conversion element to scan and drive each photoelectric conversion element. Then, the control section 36 is configured to make the signal reading circuit 17 read the electric energy accumulated in each photoelectric conversion element, and to make the signal reading circuit 17 send the read image signal to the control section 36. The control section 36 is configured to make the image storing section 18 store the sent image signal, and to make the communication section 24 send the image signal to the communication section 33 of the console 6.

Next, the operation of the radiation image radiographing system according to the present embodiment is described.

When the radiation image detector 5 is used for radiography, association is performed by the radiological technician's inputting of the identification information of a radiation image detector 5 to be used for radiography in advance in a console 6 to be used for radiography. Then, the radiation image detector 5 and the console 6 are put in the state of being associated with each other.

After that, the radiation image detector 5 accesses association information in the server 2 through the communication section 24, and grasps which of the consoles 6 on the network 7 is associated with itself. On the other hand, the radiation image detector 5 continually detects whether an association changing instruction signal including its own identification information is received.

On the other hand, the console 6 stands by until a radiography list is transmitted from the server 2 during running. When the radiography list is received through the communication section 33, the radiological technician selects a patient to be radiographed next among the patients listed in the radiography list with the input operating section 31 of the console 6, and selects a specific radiation image detector 5 to be used for the patient.

A radiography reserving instruction is thereupon input in the input operating section 31, and the control section 35 of the console 6 changes the association of the radiation image detector 5 on the basis of the input identification information. At the same time, the control section 35 transmits the input content to the communication section 24 of the radiation image detector 5 on the network 7 as an association changing instruction signal through the communication section 33.

After that, the control section 36 of the radiation image detector 5 received the association changing instruction signal including its own identification information through the communication section 24 makes the detecting means 40 confirms the progress of the operation.

The detecting means 40 confirms the progress of the operation, and transmits image data to the console 6. When the detecting means 40 detects the completion of the operation based on an instruction from the console 6 associated with itself, the detecting means outputs that effect to the control section 36, and the control section 36 makes the releasing means 41 release the association with the console 6 associated with itself. The radiation image detector 5 then becomes the state capable of performing the new association with a console 6, and the control section 36 performs the association with the console 6 (the next console 6) to which the association changing instruction signal including its own identification information and transmitted just before the confirmation of the progress of the operation by the detecting means 40. Then, the operation of the radiation image detector 5 is controlled on the basis of an instruction of the next console 6 until the association is again released by the releasing means 41.

At this time, the control section 36 of the radiation image detector 5 transmits a signal indicating the release of the association to the communication section 33 of the console 6 before the release of the association through the communication section 24.

On the other hand, when the detecting means 40 detects that the operation based on the instruction from the console 6 associated with itself has not been completed (image data has not been transmitted) at the time of confirming the progress of the operation, the detecting means outputs that effect to the control section 36, and the control section 36 controls the releasing means 41 not to release the association withy the console 6 associated with itself. The control section 36 then transmits a signal indicating that the operation is imperfect to the communication section 33 of the console 6 to which the association changing signal including its own identification information through the communication section 24.

After that, the console 6 receives the signal indicating the imperfectness of the operation through the communication section 33, and the control section 35 of the console 6 makes the display section 32 display the situation of the imperfectness of the operation of the radiation image detector 5 associated with the console 6.

After that, when the operation based on the instruction from the console 6 to which the radiation image detector 5 is associated with itself is completed, the detecting means 40 detects that effect, and outputs the effect to the control section 36. The control section 36 makes the releasing means 41 release the association with the console 6 associated with itself. The radiation image detector 5 then becomes the state capable of performing the association with a new console 6. The control section 36 then performs the association with the console 6 (the next console 6) to which the association changing instruction signal including its own identification information has been transmitted just before making the detecting means 40 confirm the progress of the operation. After that, the operation of the radiation image detector 5 is controlled on the basis of an instruction from the next console 6 until the association is again released by the releasing means 41.

As described above, according to the present embodiment, in the radiation image detector 5, the operation thereof is controlled by an associated console 6 among a plurality of consoles 6, and the detecting means 40 performs the confirmation whether the operation based on an instruction from the associated console 6 has been completed. When the detecting means 40 confirms that the operation has been completed, the radiation image detector 5 makes the releasing means 41 automatically release the association with the associated console 6. When the detecting means 40 confirms that the operation has not been completed, the radiation image detector 5 makes the releasing means 41 not automatically release the association with the associated console 6. Because the radiation image detector 5 can consequently automatically prevent the release of the association in the state in which the operation has not been completed, it can be prevented that the operation based on the instruction from the console 6 associated with the radiation image detector 5, such as the transfer of an image to the console 6, is interrupted at the time of releasing the association. Hereby, it is possible to prevent to produce unnecessary exposure to radiation owing to an error in operation, such as the disappearance of image data, which obliges a patient to receive re-radiography.

Moreover, when the association with a console 6 is released, the radiation image detector 5 itself is controlled to become capable of being associated with the next console 6. Consequently, there in no chance of the radiation image detector 5 to be associated with the next console 6 in the state of being in not released association, and the radiation image detector 5 can surely complete its operation. Consequently, the occurrence of the more unnecessary exposure to radiations to a patient can be surely prevented.

Consequently, operationality at the time of radiography can be improved.

Incidentally, it is needless to say that the present invention is not limited to the above embodiment, but can be suitably changed.

For example, although the input of the instruction of a radiography reservation is performed by selecting a radiation image detector 5 to be used for the radiography to a patient scheduled to be radiographed in the present embodiment, the configuration may be changed to be performed by selecting a patient in a radiography list if the patients to whom radiation image detectors to be used are determined in advance are listed in the radiography list.

Moreover, associate can be also detected by a console 6 by making a radiation image detector 5 provided with an IC tag pass by a sensor provided at the entrance and exit of a radiographing room so that the sensor can detect the cognitive information of the radiation image detector 5 at the time of carrying the radiation image detector 5 into the radiographing room without using manual input into the console 6 and the radiation image detector 5.

Moreover, the base station 4 can function also as the sensor. In this case, a base station 4 is provided at each certain area in the network 7, and each base station 4 can recognize the radiation image detectors 5 existing in the scope that each base station 4 manages to associate the radiation image detectors to the console associated to each base station 4.

Moreover, in the present embodiment, when the identification information of a radiation image detector 5 is input to be associated in a console 6, the console 6 transmits an association changing signal to the radiation image detector 5 to which the association is performed in the console 6. But, it is also possible to transmit an association changing signal to a console 6 that has been already associated (before a release of the association) to make the console 6 confirm the operation of the radiation image detector.

Moreover, the configuration of performing the confirmation of releasing association at the time of transmitting a signal indicating the release of the association to the console 6 before the release of the association from the radiation image detector 5 may be adopted.

Moreover, when the detecting means 40 detects the incompletion of an operation of the console 6 associated with itself as the progress of the operation, the detecting means 40 transmits a signal indicating the incompletion of the operation to the communication section 33 of the console 6 to which the association changing signal including its own identification information has been transmitted to make the console 6 received the signal display that effect. However, it may be adopted to make the control section 35 of the console 6 that has received the signal perform the control of making the operations of the input operating section 31 and the display section 32 impossible, for example, making the input from the input operating section 31 in the console 6 received the signal impossible, or display no information.

Third Embodiment

Next, a third embodiment is described.

One operation based on an instruction in a console 6 in the radiation image radiographing system 1 of the first and second embodiments transmits an image to the console 6 associated with a radiation image detector 5. On the other hand, in the third embodiment, a description is given to the case where an image is transmitted to the console associated to at least the radiation image detector 5, that is, the case where an image is transmitted to the console associated with the radiation image detector 5.

In the following, an embodiment of the present invention is described with reference to FIGS. 9-12.

Figure 9:
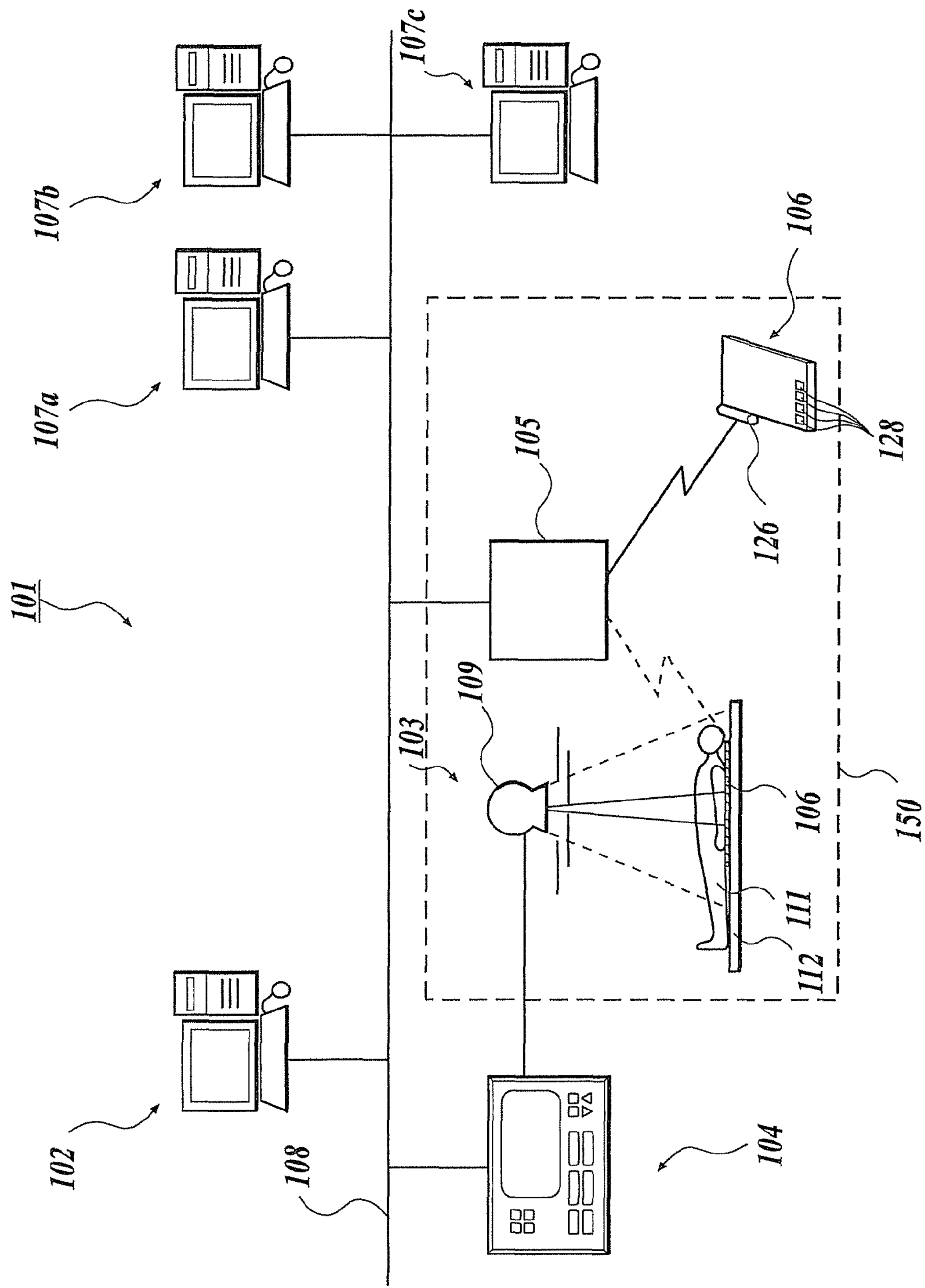
FIG. 9 is a view showing a schematic configuration illustrating a third embodiment of the radiation image radiographing system according to the present invention.

FIG. 9 is a view showing the schematic configuration of an embodiment of a radiation image radiographing system 101 to which a radiation image detector according to the present invention is applied.

The radiation image radiographing system 101 according to the present embodiment is a system performing image radiography using radiations such as an X ray. As shown in the FIG. 9, the radiation image radiographing system 101 is configured to include a server 102 managing the information pertaining to radiation image radiography, a radiation radiating operation apparatus 104 performing the operations pertaining to radiation irradiation, a base station 105 for performing communication by a wireless communication system, such as wireless local area network (LAN), and consoles 107$a$, 107$b$, and 107$c$ for managing a radiographing room 150 and for operating a radiation image detector 106 installed in the radiographing room 150, all of which are mutually connected through a network 108 to be able to transmit and receive information with one another. A radiation tube 109 radiating a radiation to a patient 111 who is a subject is connected to the radiation radiating operation apparatus 104 through a cable. Incidentally, the radiation used of radiography is not limited to an X ray, but the X ray is most suitably used. If the X ray is used for radiography, an X-ray tube radiating X rays are sued as the radiation tube 109, and an X-ray image detecting apparatus is used as the radiation image detector 106.

Incidentally, the number of the consoles connected to the network 108 is not limited to three, but furthermore a plurality of consoles may be connected. Moreover, the number of the radiographing rooms 150 is not limited to the one shown in the drawing, but a plurality of radiographing rooms 150 may be installed. The radiographing rooms 150 and the consoles 107 may be associated one-on-one, or one console 107 may be associated with a plurality of radiographing rooms 150 to manage the plurality of radiographing rooms 150 by one console 107. Moreover, a plurality of consoles 107 may be associated with one radiographing room 150.

Now, the network 108 may be a communication line dedicated for the system, but it is more preferable that the network 108 is the existing lines such as Ethernet (registered trademark) from the reasons of reducing the flexibility of the system configuration.

Figure 10:
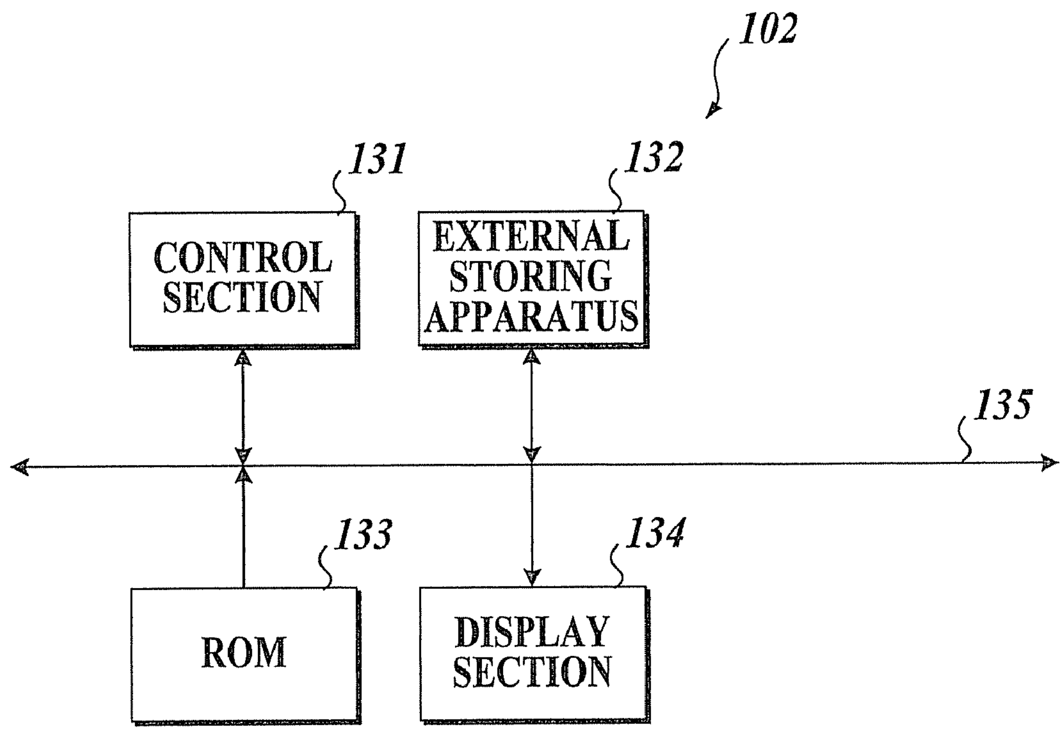
FIG. 10 is a block diagram showing the configuration of the principal part of a server constituting the radiation image radiographing system of the FIG. 9.

The server 102, as shown in FIG. 9, is composed of a computer. As shown in FIG. 10, the server 102 is provided with a control section 131 controlling each section constituting the server 102, an external storing apparatus 132 storing various kinds of information, an input operating section 133 inputting various kinds of information and instructions of an operator, a display section 134 displaying input information and the like, and the like. Each section is mutually connected by a bus 135.

The input operating section 133 is composed of, for example, a keyboard, a mouse, and the like, and outputs a depression signal of a key operated by depression on the keyboard and an operation signal by the mouse to the control section 131 as an input signals.

In particular, in the radiation image radiographing system 101 according to the present embodiment, the input operating section 133 is configured to perform the input of patient information, radiography information, and the like, as patient information inputting means, the registration of the patient 111 to be scheduled to be radiographed is hereby performed. Incidentally, the information input with the input operating section 133 is not limited to the ones illustrated here.

The patient information is the information pertaining to the patient 111, such as the name, the age, the sex, and the date of birth of the patient 111, and the patient ID number for specifying the patient 111. Moreover, the radiography information is the information for performing radiography, such as a radiography region (the part to be radiographed in a body of the patient 111), radiography conditions such as a tube voltage and an irradiation dose (mAs value), and the direction and the method of radiography. Moreover, for example, if a plurality of times of radiography is performed to one patient 111, the number of scheduled radiography times and the like are also input as the radiography information.

Incidentally, the patient information and the radiography information are not limited to those input with the input operating section 133 of the server 102 as described above. For example, the information input from the consoles 107 and transmitted to the server 102 may be used. Moreover, for example, the information input from a not-shown other terminal apparatus, such as a personal computer, installed in a consultation room of a doctor or the like and connected to the network 108 may be received by the server 102. Furthermore, the input may be performed by providing an information reading apparatus, such as a card reader, for reading the patient information and the radiography information that have been written in an ID card or the like in advance, and by reading the patient information and the radiography information with such an information reading apparatus. In these cases, each of the input means, the information reading apparatus, and the like, constitutes the patient information inputting means.

The control section 131 is composed of, for example, a central processing unit (CPU), and is configured to read various programs stored in the external storing apparatus 132 and the like, and to execute various kinds of processing in accordance with the various programs.

In particular, in the present embodiment, the control section 131 generates as patient list generating means a list in which the information input with the input operating section 133, and patient information and radiography information that have been input with an external apparatus, such as the consoles 107, and sent through the network 108 are mutually associated (herein after referred to as "patient list"), and makes the external storing apparatus 132 store the generated patient list. The patient list generated by the control section 131 of the server 102 is shared by each of the consoles 107 through the network 108. Incidentally, if new information is input from the input operating section 133 or the like after a patient list has been once generated, then the patient list is sequentially updated, and the updated patient list is shared by the server 102 and each of the consoles 107.

Moreover, the radiation image information detected by each of the radiation image detectors 106 and transmitted to the consoles 107 is sent to the server 102 in the state of being associated with the patient information of the radiographed patient, the information for identifying what number image of the radiographed ones of the patient the radiation image information is, the other radiography information pertaining to radiography, and the like. Incidentally, besides these pieces of information, for example, the identification information for identifying which console 107 operates the radiation image detector 106 with which radiography is performed at the time of the radiography, and the like, may be associated with the radiation image information sent from the radiation image detector 106 to the server 102. The control section 131 makes the external storing apparatus 132 or the like store the sent information together with the radiation image information in the state of being associated with the patient list, and manages the information.

When the radiation image information associated with the patient information and the radiography information is sent to the control section 131, the control section 131 performs the retrieval of whether the past radiation image information associated with the same patient information and the like exists in the radiation image information stored in the external storing apparatus 132. The past radiation image information may be the whole of the radiation image information that has been radiographed and has been associated with the same patient information, or may be the radiation image information that has been already radiographed in the radiographing schedule of the patient if a plurality of times of radiography of the same patient and a series of radiography schedule is associated with the patient list, for example, here.

Moreover, the control section 131 as image information transmitting means transmits the radiation image information associated with the same patient information among the pieces of radiation image information based on the detection results of the radiation image detector 106 to the console 107 associated as the console 107 operating the radiation image detector 106 that has radiographed the patient last at the time of radiography.

The radiography that has been performed last means the last radiography among the series of radiography scheduled for a certain patient here. That is, for example, if four times of radiography are scheduled as a series of radiography for a certain patient, the radiography at the second time is the last radiography when the second radiography ended. Consequently, in this case, the radiation image information obtained by the first radiography is sent to the console 107 associated as the console 107 operating the radiation image detector 106 that was used for the second radiography at the radiography. Similarly, if four times of radiography are scheduled, the fourth radiography is the last radiography when the fourth radiography ended. Consequently, the radiation image information obtained at the first to the third radiography is sent to the console 107 associated as the console 107 operating the radiation image detector 106 used at the fourth radiography at the time of radiography.

Consequently, for example, when the four times of radiography of a certain patient were scheduled and the fourth radiography was performed as mentioned above, and when the radiation image information is sent to the control section 131 in the state of being associated with the patient information and the radiography information, the control section 131 performs retrieval in the external storing apparatus 132 on the basis of the patient information and the like. Then, the control section 131 selects the radiation image information obtained by the first to the third radiography of the patient as the result of the retrieval, and transmits the radiation image information to the console 107 as the console 107 operating the radiation image detector 106 used for the fourth radiography at the time of radiography.

Incidentally, the radiation image information to be transmitted to the console 107 is the radiation image information that was already radiographed in the radiography schedule of the patient, for example, if a plurality of times of radiography of different radiography regions of the same patient is scheduled and a series of radiography schedule is associated with the patient list. That is, for example, if four times of radiography schedule of the front of the abdominal region, the side of the abdominal region, the front of the chest region, and the side of the chest region are associated with the patient list, and when the radiography of the front of the abdominal region, the side of the abdominal region, and the front of the chest region ended, and furthermore when the side of the chest region was radiographed, then the radiation image information of the front of the abdominal region, the side of the abdominal region, and the front of the chest region, the radiography of all of which already ended, is transmitted to the console 107 associated as the console 107 operating the radiation image detector 106 at the time of the radiography of the side of the chest region.

Moreover, for example, if a plurality of times of radiography of the same part of the same patient is scheduled, for example, if three times of radiography of the abdominal region and three times of radiography of the chest region are scheduled for observing the changes with time of the same parts, and if radiography has been performed until the second radiography of the abdominal region and the second radiography of the chest region, and further if the third radiography of the chest region of the patient has been performed and the radiation image information has been transmitted from the console 107 together with the patient information and the like, then only the first and the second radiation image information of the chest region, which pertains to the same part in the radiography schedule of the patient and has been already radiographed, may be transmitted to the predetermined console 107.

Furthermore, the whole of the radiation image information coinciding with the patient information or the like associated with the radiation image information sent to the control section 131 may be transmitted to the console 107, or, for example, only the radiation image information until an arbitrary number of times of radiography from the newest date of radiography in order among the pieces of the radiation image information with which the patient information coincides may be transmitted to the console 107.

Moreover, at this time, the radiation image information transmitted from the control section 131 to the console 107 may be both the original image information and a displaying image, but it is preferable to transmit only the displaying image, which has a small information quantity, for performing the transfer the information smoothly and for performing the confirmation of the image in the console 107 quickly.

Next, a radiation image radiographing apparatus 103 is configured to include the radiation tube 109 radiating radiations to function as a radiation radiating apparatus, and is configured to radiate the radiations from the radiation tube 109 by the tube voltage and the irradiation dose that have been set with the radiation radiating operation apparatus 104. A bed 112 on which the patient 111 is placed is provided below the radiation tube 109 in the scope of the radiation irradiation, and the radiation image detector 106 reading the radiations to detect a radiation image is disposed at the position corresponding to the radiography region of the patient 111 when the patient 111 is placed thereon, which position is on the bed 112. Incidentally, the position where the radiation image detector 106 is disposed is not limited to the position between the patient 111 and the bed 112, but there may be adopted, for example, the configuration where a detecting apparatus connecting port (not shown) connecting the radiation image detector 106 therein is formed in the lower part of the bed 112 and the radiation image detector 106 is connected into the detecting apparatus connecting port.

The radiation radiating operation apparatus 104 is composed of a computer including a display section displaying information, an input operating section (both of which are not shown) inputting an instruction from a radiological technician, who is an operator, and the like. The radiation radiating operation apparatus 104 is configured to control the radiation tube 109 and the like of the radiation image radiographing apparatus 103 so that radiography may be performed at a tube voltage value and a radiation dose that correspond to the input radiography conditions.

Figure 11:
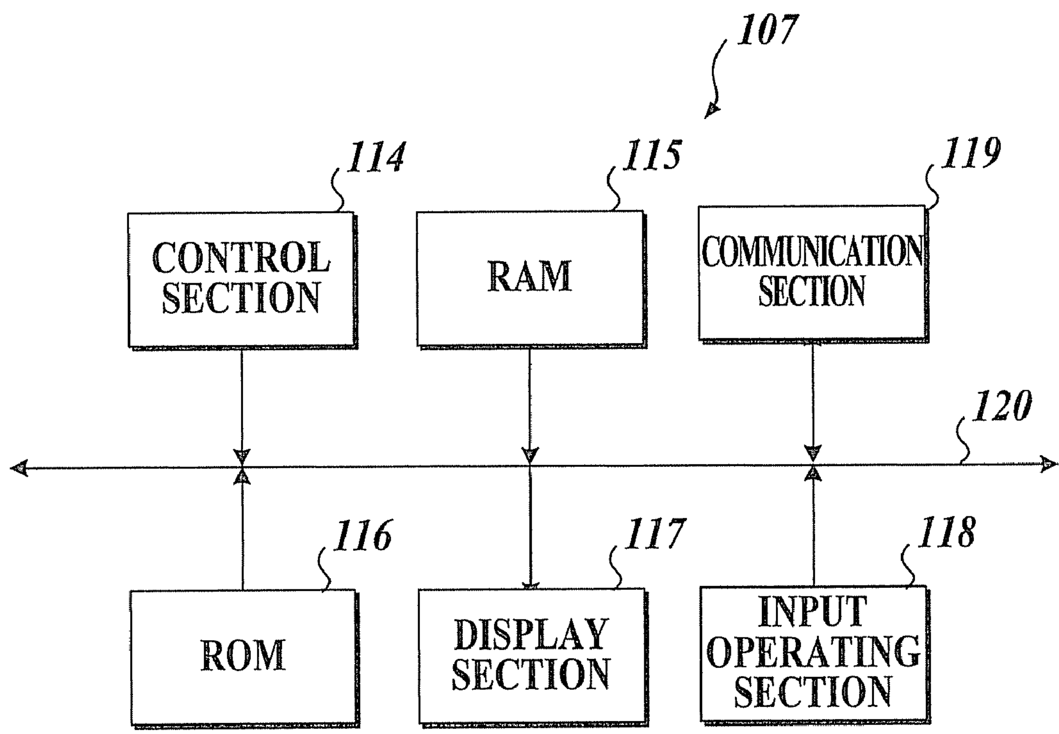
FIG. 11 is a block diagram showing the configuration of the principal part of a console constituting the radiation image radiographing system of the FIG. 9.

Next, as shown in FIG. 11, each of the consoles 107 is configured to include a control section 114 composed of a central processing unit (CPU) and the like, a random access memory (RAM) 115, a read only memory (ROM) 116, a display section 117, an input operating section 118, a communication section 119, and the like. Each unit is mutually connected by a bus 120. In the present embodiment, as mentioned above, the plurality of consoles 107*a*, 107*b*, and 107*c* are connected to the network 108. For example, a console ID is given to each of the consoles 107*a*, 107*b*, and 107*c* as identification information for identifying the consoles 107*a*, 107*b*, and 107*c*.

The display section 117 is configured to include, for example, a cathode ray tube (CRT), a liquid crystal display (LCD), or the like, and displays various screens, such as patient lists, various messages, various images, and the like, according to the instructions of display signals sent from the control section 114.

The input operating section 118 is composed of, for example, a keyboard and a mouse. The input operating section 118 outputs a depression signal of a key the depression operation of which has been performed with the keyboard, and an operation signal of the mouse to the control section 114 as input signals. Incidentally, the input operating section 118 may be configured of the so-called touch panel, which outputs the positional information input by touching a transparent sheet panel covering the display screen of the display section 117 with a finger or a dedicated stylus pen to the control section 114 as an input signal.

In particular, in the radiation image radiographing system 101 according to the present embodiment, the input operating section 118 is configured to be able to input patient information, radiography information, the detecting apparatus ID of the input and radiation image detector 106, and the like. The detecting apparatus ID is the identification information of the radiation image detector 106, which identification information is given to each radiation image detector 106 for identifying the radiation image detector 106, here.

The console 107 to which the identification information of the radiation image detector 106 is input is, for example, the console 107 managing the radiographing room 150 in which the radiation image detector 106 is installed. The position where the console 107 managing the radiographing room 150 is installed is not specially limited, but it is preferable to be the console 107 installed at the nearest position to the radiographing room 150 and the radiation radiating operation apparatus 104. By setting the console 107 in this manner, it becomes possible to perform the operation of the radiation image detector 106 in the radiographing room 150 from the nearest position to the radiographing room 150 and the radiation radiating operation apparatus 104 at the time of performing radiography.

Moreover, the display section 117 is configured to display a patient list transmitted from the server 102 through the network, and the input operating section 118 is configured to be able to select the patient to be radiographed and the radiography region in the patient list as patient selecting means. Incidentally, the patient list is not limited to the one transmitted from the server 102, but the system capable of reading the patient list stored in the server 102 to refer to it. The information of the patient, the radiography region, and the like selected by the input operating section 118 is associated with the identification information of the console 107 that has selected them, and is sent to the server 102 through the network 108.

Moreover, if there is a plurality of radiation image detectors 106 associated with the console 107, the input operating section 118 is configured to be able to select the radiation image detector 106 to perform radiography.

Hereby, the setting of the radiation image detector 106 to radiographing a patient is performed before the radiography. Incidentally, when the setting has been performed, the other consoles 107 may be configured to be unable to select the patient in the patient list.

Moreover, the input operating section 118 outputs a signal according to a transfer instruction of the radiation image information based on a detection result of the radiation image detector 106 to the control section 114 on the basis of a predetermined operation. In the present embodiment, the radiation image information obtained by radiography is associated with the radiation image detector 106 used for the radiography, and is transferred to the console 107 that has operated the radiation image detector 106 at the time of the radiography. And the radiation image information is, as will be described later, associated with the patient information, the radiography information, and the like, of the patient selected in the patient list by the control section 114 of the console 107 at the time of setting before the radiography. The radiation image information associated with the patient information, the radiography information, and the like, is transferred to the server 102, and is saved in a not-shown storage apparatus or the like as the occasion demands. Incidentally, the radiation image information associated with the patient information, the radiography information, and the like, may be transmitted to an external apparatus other than the server 102 as the occasion demands.

Moreover, the input operating section 118 outputs a signal according to a deletion instruction of the radiation image information stored in the radiation image detector 106 to the control section 114 on the basis of the predetermined operation.

Moreover, if a radiological technician performs the judgment of whether a subject image is properly detected by the radiation image detector 106 and the judgment of the necessity of re-radiography, then the input operating section 118 inputs the judgment result. The input result is output to the control section 114 as an electric signal.

The communication section 119 performs the communications of various kinds of information with the radiation image detector 106 through the base station 105 by a wireless communication system, such as a wireless LAN.

The control section 114 is composed of, for example, a central processing unit (CPU) as mentioned above, and is configured to read a predetermined program stored in the read only memory (ROM) 116, to expand the read program in the working area of the random access memory (RAM) 115, and to execute various kinds of processing according to the program.

In particular, in the present embodiment, when a detecting apparatus ID is input from the input operating section 118 as the identification information of the radiation image detector 106, the input detecting apparatus ID is sent to the control section 114 as a signal. The control section is configured so that, when the control section 114 obtains the detecting apparatus ID, the control section 114 associates the detecting apparatus ID with the a console ID to perform the association of the radiation image detector 106 with the console 107 as console associating means.

To put it concretely, for example, when the detecting apparatus ID of the radiation image detector 106 is input from the input operating section 118 of the console 107*a*, the control section 114 associates the console 107*a* as the console 107 operating the radiation image detector 106 having the detecting apparatus ID at the time of radiography.

Incidentally, the input system for the control section 114 to identify the radiation image detector 106 that is associated with the console 107 is not limited to the one shown here, but the input system may be the one of attaching, for example, an IC tag or a bar code to the radiation image detector 106 as the identification information for identifying the radiation image detector 106, and of reading the IC tag or the bar code with a predetermined reading apparatus or the like. Consequently, the identification information of the radiation image detector 106 is input, and the control section 114 obtains the identification information.

Moreover, the timing when the control section 114 obtains the identification information of the radiation image detector 106 by the input of the detecting apparatus ID from the input operating section 118 or the like and performs the association of the radiation image detector 106 with the console 107 is preferably performed, for example, at the time when the radiation image detector 106 is carried into the radiographing room 150, but the timing of the association is not limited to this timing.

Incidentally, if the radiation image detector 106 has been once associated with a certain console 107 and moves from the radiographing room 150 where the radiation image detector 106 has been initially installed to another radiographing room 150 after that, then the re-association of the radiation image detector 106 with a new console 107 is performed by the control section 114 of the console 107 managing the moving destination radiographing room 150 by the input of the detecting apparatus ID of the radiation image detector 106 from the input operating section 118 of the console 107 managing the moving destination radiographing room 150, or the like. Incidentally, when a new correspondence relation between the console 107 managing the radiographing room 150 of the moving destination and the radiation image detector 106 has been formed, the correspondence relation with the console 107 that has been previously associated is released.

To put it concretely, for example, when a radiation image detector 106 is carried in a certain radiographing room 150 and a detecting apparatus ID is input from the input operating section 118 of the console 107 managing the radiographing room 150, the control section 114 associates the console 107*a* as the console 107 operating the radiation image detector 106 at the time of radiography. After that, when the radiation image detector 106 moves to another radiographing room 150 and the console 107*b* manages the radiographing room 150, a detecting apparatus ID of the radiation image detector 106 is input from the input operating section 118 of the console 107*b*, and the control section 114 associates the console 107*b* as the console 107 operating the radiation image detector 106 at the time of radiography. When a new correspondence relation between the console 107*b* and the radiation image detector 106 is formed, the correspondence relation between the console 107*a*, with which the association has been performed previously, and the radiation image detector 106 is released.

Moreover, the control section 114 performs the association of the radiography information including the information of what number image of the radiographed ones of the patient the patient information and the radiation image information of the radiographed patient is, and the like, and the radiation image information based on a detection result by the radiation image detector 106, as patient information associating means. Incidentally, the information associated with the radiation image information by the control section 114 is not limited to these pieces of information. For example, the identification information for identifying which console 107 operates the radiation image detector 106 with which radiography is performed at the time of the radiography, and the like, may be associated.

The control section 114 is configured to send the radiation image information to which the patient information and the like are associated to the server 102 through the network 108.

Moreover, the control section 114 is configured to be able to also wirelessly transmit the information necessary for radiography, such as the information pertaining to a radiography region, to the radiation image detector 106 through the base station 105.

The control section 114 is configured so that the radiation image information obtained by the radiation image detector 106 may be sent. When the control section 114 receives the radiation image information, the control section 114 generates a displaying image having reduced image information of an information quantity smaller than that of the original image information, such as the so-called thumbnail image, on the basis of the sent radiation image as displaying image generating means. The reduction ratio of the reduced image is preferably, for example, the degree by which the length of each side becomes ½-1/100 times of that of the original image (the degree by which the number of pixels becomes ¼-1/10000 times of that of the original), and the degree of ¼-1/2500 times is more preferable.

Moreover, the control section 114 makes the display section 117 suitably display various kinds of information and images on the basis of an instruction input from the input operating section 118 or the like. Incidentally, when an input indicating not to perform any re-radiography is input from the input operating section 118, it is preferable to make the display section 117 display the patient information and the radiography information according to the radiography to be performed next.

Furthermore, the control section 114 transmits a signal instructing the deletion of the radiation image information stored in the radiation image detector 106 on the basis of a signal according to a deletion instruction input form the input operating section 118 to the radiation image detector 106 to make the radiation imaged detector 106 delete the radiation image information.

Figure 12:
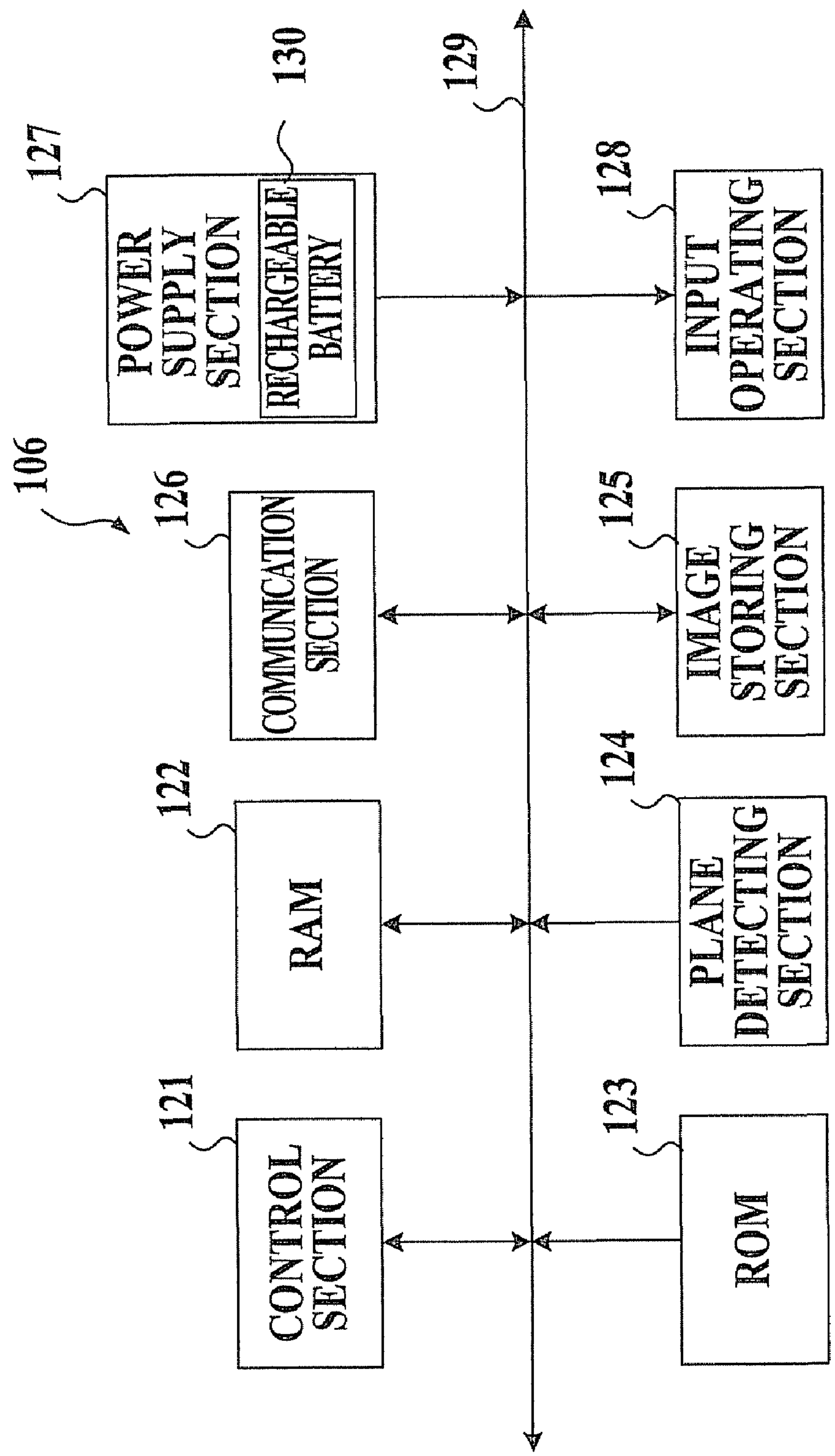
FIG. 12 is a block diagram showing the configuration of the principal part of the radiation image detector constituting the radiation image radiographing system of the FIG. 9.

Next, the radiation image detector 106 is, for example, a portable cassette shaped FPD, and the radiation image detector 106 is configured to include, as shown in FIG. 12, a control section 121, a RAM 122, a ROM 123, a plane detecting section 124, which is a radiation detecting section, an image storing section 125, which is storage means, a communication section 126, a power supply section 127, an input operating section 128, and the like. Each section is mutually connected by a bus 129.

A detecting apparatus ID is given to each radiation image detector 106 as identification information for identifying each radiation image detector 106. Incidentally, the identification information for identifying each radiation image detector 106 is not limited to the detecting apparatus ID as mentioned above, and, for example, may be an IC tag or a bar code.

The plane detecting section 124 includes, for example, a glass board and the like. A plurality of pixels detecting the radiations that have been radiated from the radiation tube 109 and have transmitted at least a subject according to their intensities, the pixels converting the detected radiations into electric signals to accumulate the converted electric signals, is arranged in a matrix on the predetermined positions of the board.

As the plane detecting section 124, for example, an indirect type one including a radiation/light converting layer converting radiation into fluorescence (light), and a photoelectric conversion layer detecting the fluorescence converted by the radiation/light converting layer to convert the detected fluorescence into an electric signal, a direct type one including a radiation/electric signal converting layer having a radiation receiving section converting radiation into electric charges directly in place of the radiation/light converting layer and the photoelectric conversion layer, or the like can be cited here, although they are not shown. Incidentally, because the indirect type one does not need a high-voltage power source, which is used in the direct type one, the indirect type one is preferable.

The image storing section 125 is composed of a nonvolatile memory, such as a flash memory, or a RAM, and can store the radiation image information obtained by the reading of the electric signal accumulated in the plane detecting section 124. The storage capacity of the image storing section 125 is not especially limited, but it is preferable to be a capacity capable of storing a plurality of pieces of radiation image information. The capacity capable of storing the plurality of pieces of radiation image information in this manner enables the next radiography without transferring radiation image information to an external apparatus, such as the consoles 107 and the server 102, or without waiting the judgment of the suitability of radiography, and enables raising the working efficiency of the apparatus.

The communication section 126 performs the communicates of various kinds of information with the consoles 107 by a wireless communication system, such as a wireless LAN, through the base station 105. For example, the communication section 126 receives various kinds of information, such as the patient information and the radiography information transmitted from the communication sections 119 of the consoles 107, and a console ID of the console 107 associated with the radiation image detector 106. Moreover, the communication section 126 transmits the detecting apparatus ID of the radiation image detector 106 to the console 107. Then, the communication section 126 is configured to transmit the radiation image information stored in the image storing section 125 to the console 107 associated with the radiation image detector 106. Furthermore, the communication section 126 receives a radiography suitability signal pertaining to the suitability of the radiography state of a radiation image transmitted through the communication section 119 of the console 107, a deletion instruction signal instructing the deletion of radiation image information stored in the radiation image detector 106, and the like.

The power supply section 127 includes a rechargeable battery 130 as the power supplying means for supplying a power source to each unit constituting the radiation image detector 106, and is configured to be chargeable through a charging terminal (not shown) provided at a predetermined position of the radiation image detector 106.

The control section 121 is composed of, for example, a CPU and the like, and reads a predetermined program stored in the ROM 123 to expand the read program in the working area of the RAM 122. Then, the control section 121 executes various kinds of processing according to the program.

To put it concretely, for example, the control section 121 controls a switching section, such as a thin film transistor (TFT), constituting each pixel of the plane detecting section 124 to proceed the switching of the reading of electric signals accumulated in each pixel, and to read the electric signals accumulated in the plane detecting section 124. Thereby, the control section 121 obtains a detection result from the plane detecting section 124.

Furthermore, the control section 121 controls the communication section 126 to transmit the detecting apparatus ID of the radiation image detector 106 to the console 107. Moreover, the control section 121 controls the communication section 126 to transmit the radiation image information based on a detection result detected by the radiation image detector 106 to the console 107 as the image information transmitting means.

In the present embodiment, the destination of the transmission of radiation image information by the control section 121 through the communication section 126 is the console 107 associated as the console 107 operating the radiation image detector 106 at the time of radiography. At least the identification information, such as the detecting apparatus ID, of the radiation image detector 106 that has performed radiography is given to the radiation image information to be transmitted to the console 107 as accompanying information. Furthermore, the patient information and the radiography information that are associated with the patient list, a console ID of the console 107 associated as the console 107 operating the radiation image detector 106 at the time of radiography, and the like, may be included. Moreover, the input operating section 118 may be configured to enable the input of the timing of transferring the radiation image information from the radiation image detector 106. Incidentally, the timing of transferring the radiation image information from the radiation image detector 106 is preferably as soon as possible.

Next, the operation of the radiation image radiographing system 101 is described.

When a radiation image detector 106 is newly installed in a radiographing room 150, a radiological technician inputs the identification information, such as the detecting apparatus ID, of the radiation image detector 106 with the input operating section 128 or the like of the console 107*a* managing the radiographing room 150. When the identification information, such as the detecting apparatus ID, is input, the association of the console 107*a* with the radiation image detector 106 is performed by the control section 114. When the association is performed, the console ID of the console 107*a* and the detecting apparatus ID of the radiation image detector 106 are sent to the server 102 in the state of being associated with each other through the network 108, and the console ID and the detecting apparatus ID are stored in the external storing apparatus 132 or the like of the server 102.

On the other hand, when the patient information, the radiography information, and the like, are input from any one of the consoles 107, each of the input information is sent to the server 102 through the network 108. When the patient information, the radiography information, and the like, are sent, a patient list associating each information is generated by the control section 131 of the server 102. Incidentally, the patient information, the radiography information, and the like may be transmitted from various information reading apparatus, such as the input operating section 133 of the server 102 and an ID card reader, a terminal apparatus, which is installed in a consultation room and is connected to the network 108, and the like besides being input from the consoles 107.

A the time of performing the radiography of a radiation image, a radiological technician first goes to the console 107*a* associated with the radiographing room 150 in which radiography is performed, and refers to the patient list stored in the server 102 through the network 108 to make the display section 117 of the console 107*a* display the patient list. Then, the radiological technician selects a patient 111 to be radiographed, and a radiography region and the like as the occasion demands in the patient list. If a plurality of radiation image detectors 106 is installed in the radiographing room 150, the radiological technician further selects a radiation image detector 106 to be used for the radiography among the radiation image detectors 106 installed in the radiographing room 150 with the input operating section 118.

Next, the patient information and the radiography information are transmitted from the server 102 to the consoles 107 and the radiation radiating operation apparatus 104. The patient information and the radiography information are suitably displayed on the display section 117 of the consoles 107, and the radiological technician confirms these pieces of information while performing the radiography of a radiation image while.

The radiation radiating operation apparatus 104 controls the radiation tube 109 of the radiation image radiographing apparatus 103 on the basis of the tube voltage value, the radiation quantity, and the like, included in the received radiography information, and the radiation image radiographing apparatus 103 radiates radiations to the patient 111 under these conditions.

At this time, the radiation image detector 106 is inserted into the position between the patient 111 and the bed 112, and detects the quantity of the radiations that have transmitted the patient 111. Then the radiation image detector 106 converts the detected radiations into an electric signal to obtain a predetermined detection result, which is stored in the image storing section 125.

Moreover, the detection result detected by the radiation image detector 106 is transmitted to the console 107*a* associated with the radiation image detector 106 as the console 107 operating the radiation image detector 106 at the time of radiography in the state of being associated with the detecting apparatus ID of the radiation image detector 106 used for the radiography by the control section 121.

The control section 114 of the console 107*a* generates a displaying image such as the so-called thumbnail image having a smaller information quantity than that of the original image information on the basis of the sent detection result as the displaying image generating means, and makes the display section 117 display the generated displaying image. The radiological technician performs the judgment of whether the subject image is properly detected by the radiation image detector 106 and the necessity of re-radiography by confirming the displaying image.

If the subject image is properly detected and the re-radiography is unnecessary, the control section 114 of the console 107*a* associates the original image information with the patient information and the like through the communication section 119 to transmit the associated information to the server 102. After that, the original image information receives image processing by the server 102, and then is suitably output from an output apparatus, such as a printer or a monitor, to be supplied to a diagnosis of a doctor as a radiation image. On the other hand, the displaying image is deleted by the control section 114.

Moreover, the control section 114 transmits a signal indicating that the radiography state of the radiation image is proper and a deletion instruction signal instructing the deletion of the detection result stored in the radiation image detector 106 to the radiation image detector 106. The control section 121 of the radiation image detector 106 receives these signals to delete the detection result from the image storing section 125, and ends the radiography by the radiation image detector 106. In this case, the patient information, the radiography information, and the like, of the next radiography are then suitably displayed on the display section 117 of the console 107*a*.

On the other hand, if the subject image has not been properly detected and a signal indicating the necessity of re-radiography is input from the input operating section 118, the original image information and the displaying image are deleted, and an instruction instructing the performance of the re-radiography is transmitted to the radiation radiating operation apparatus 104. Hereby, the re-radiography is performed, and a detection result detected by the radiation image detector 106 is again transmitted to the console 107*a*. The control section 114 of the console 107*a* generates a displaying image having an information quantity smaller than that of the original image information on the basis of the sent detection result, and makes the display section 117 display the generated displaying image. If the subject image has been properly detected and the necessity of the re-radiography does not exist, the control section 114 of the console 107*a* associates the original image information with the patient information and the like through the communication section 119 to transmit the associated information to the server 102. Moreover, the control section 114 of the console 107*a* deletes the displaying image similarly to the above, and transmits a signal indicating that the radiography state of the radiation image is proper and a deletion instruction signal instructing the deletion of the detection result stored in the radiation image detector 106 to the radiation image detector 106 to end the series of radiography operations.

Incidentally, if the radiation image detector 106 moves into another radiographing room 150 after that, the identification information, such as the detecting apparatus ID, of the radiation image detector 106 is input from the input operating section 128 of the console 107*b* managing the radiographing room 150, for example, when the radiation image detector 106 is carried into the radiographing room 150 of the moving destination. When the identification information is input, the control section 114 associates the console 107*b* with the radiation image detector 106, and on the other hand the association of the console 107*a* associated previously with the radiation image detector 106 is released. When the association of the console 107*b* with the radiation image detector 106 is performed, the console ID of the console 107*b* and the detecting apparatus ID of the radiation image detector 106 are sent to the server 102 through the network 108 in the state of being associated with each other, and the new association is stored in the external storing apparatus 132 or the like of the server 102.

Then, when the next radiography is performed in the radiographing room 150 of the moving destination, the radiation image detector 106 is operated by the console 107*b* at the time of the radiography, and a detection result detected by the radiation image detector 106 is transmitted to the console 107*b*. Furthermore, a displaying image is generated by the control section 114 of the console 107*b* to be displayed on the display section 117 of the console 107*b*.

Incidentally, radiography may be performed a plurality of times while moving in the radiographing rooms 150. In this case, before each radiography, the radiation image detector 106 to be used for the radiography is associated with the console 107 operating the radiation image detector 106, and a detection result obtained by the radiation image detector 106 is sent to the associated console 107 at the time of each radiography.

As described above, by the radiation image radiographing system 101 according to the present embodiment, the detection result detected by the radiation image detector 106 is transmitted to the previous console 107 of the radiographing room 150 associated in advance at the time of the radiography, and a displaying image is generated by the console 107 to be displayed on the display section of the console 107. Consequently, even if the input of the patient information and the radiography information and the association of the radiation image detector 106 with the console 107 are performed by any console 107, the radiographed image can be confirmed with a console 107 situated near to the radiographing room 150 used for the radiography, and the radiological technician can instantly and surely confirm whether the subject image is properly detected without moving to a position distant from the radiographing place to judge the suitability of the radiation image. Consequently, the operationality at the time of radiography can be improved.

Moreover, in the present embodiment, after the detection result detected by the radiation image detector 106 has been transmitted to the corresponding console 107, the control section 114 of the consoles 107 generates a displaying image, but the displaying image generating means for generating the displaying image is not limited to the case where it is the control section 114 of the console 107.

For example, as the present embodiment, if the radiation image detector 106 is a cassette shaped FPD, the displaying image may be generated by the control section 121 of the radiation image detector 106. In this case, the original image information and displaying image that have been generated by the control section 121 of the radiation image detector 106 may be sent to the console 107 or to the server 102 by wireless communication means or the like. Furthermore, only the displaying image may be sent to the console 107, and the original image information may be sent to the server 102. Moreover, the original image information may be stored in the image storing section 125 of the radiation image detector 106, and only the displaying image may be sent to the consoles 107. In this case, when a signal indicating that the radiography state of a radiation image is proper is sent from the console 107 to the radiation image detector 106, the original image information may be transmitted to the console 107 or the server 102. Moreover, the detection result of the radiation image detector 106 may be directly sent to the server 102, and a displaying image may be generated in the server 102 besides the original image information.

In the present embodiment, the control section 114 of the radiation image detector 106 transmits the radiation image information to the predetermined console 107 through the communication section 119 as the image information transmitting means, but the image information transmitting means is not limited to this mode. For example, as described above, the detection result by the radiation image detector 106 may be directly sent to the server 102. And, if a displaying image is generated in the server 102 in addition to the original image information, then the control section 131 of the server 102 transmits the original image information and the displaying image, or only the displaying image to the console 107 as the image information transmitting means.

Incidentally, in this case, the detection result of the radiation image detector 106 is sent to the server 102, for example, in the state of being associated with the detecting apparatus ID of the radiation image detector 106 used for the radiography. The control section 131 of the server 102 collates the sent detecting apparatus ID with the detecting apparatus ID stored in the external storing apparatus 132, and transmits the radiation image information to the console 107 having the console ID associated with the coinciding detecting apparatus ID. Incidentally, the detection result to be sent from the radiation image detector 106 to the server 102 may be associated not only with the detecting apparatus ID of the radiation image detector 106 used for the radiography, but only with the console ID of the console 107 that has operated the radiation image detector 106 at the time of the radiography. In this case, the radiation image information is transmitted to the console 107 corresponding to the console ID.

Incidentally, although a patient list is generated in the control section 131 of the server 102 in the present embodiment, the main component of the generation of the patient list is not limited to this one. For example, the patient list may be generated in the control section 114 of the console 107; the generated patient list may be sent from the console 107 to the server 102 to be stored in the external storing apparatus 132 or the like of the server 102; and the patient list may be transmitted from the server 102 to each console 107 to be shared by them.

Incidentally, in the present embodiment, if, after the radiation image detector 106 has been once associated with a certain console 107, the radiation image detector 106 is newly associated with another console 107 owing to the shifting of the radiographing room 150, then the association of the previously associated console 107 with the radiation image detector 106 is released. But, if the new association of the radiation image detector 106 with the other console 107 is formed owing to the shifting of the radiographing room 150 or the like, the previous associate may not be released, and a plurality of associations may duplicate. In this case, for example, by associating the radiation image obtained by the radiation image detector 106 with the console ID of the console 107 that has operated the radiation image detector 106 at the time of the radiography, the radiation image is transmitted only to the console 107 having the console ID. Hereby, the image can be transmitted only to the console 107 that has operated the radiation image detector 106 at the time of the radiography, and the image can be immediately confirmed in the vicinity of the radiographing room 150 after the radiography. Consequently, such an association is convenient.

Fourth Embodiment

Next, a fourth embodiment is described.

In the fourth embodiment, a description is given to the other patterns of the operations based on an instruction of a console in the radiation image radiographing system 101 described pertaining to the third embodiment. In the following description, the description is performed with the operation of the radiation image radiographing system 101 focused. The similar portions as those of the third embodiment is not described in detail, and the similar portions are described by denoting them by the same marks as those of the third embodiment.

The radiation image radiographing system in the fourth embodiment is configured similarly to the radiation image radiographing system 101 in the third embodiment. Next, the operation of the radiation image radiographing system is described.

When a new radiation image detector 106 is installed in the radiographing room 150, a radiological technician inputs the identification information, such as the detecting apparatus ID, of the radiation image detector 106 with the input operating section 128 or the like of the console 107*a* managing the radiographing room 150. When the identification information, such as the detecting apparatus ID, has been input, the control section 114 associates the console 107*a* with the radiation image detector 106. When the association has been performed, the console ID of the console 107*a* and the detecting apparatus ID of the radiation image detector 106 are sent to the server 102 through the network 108 in the state of being associated with each other, and are stored in the external storing apparatus 132 or the like of the server 102.

On the other hand, when patient information, radiography information, and the like, are input from any of the consoles 107, each of the input information is sent to the server 102 through the network 108. At this time, the number of scheduled radiography times is also input as the radiography information. If radiography of radiation images is performed, for example, four times to one patient, then the number of times of radiography is registered as four. Incidentally, the number of times of radiography and the like can be suitably changed by performing the inputs of addition or modification later with the input operating section 118, the server 102, or the like.

When the patient information, the radiography information, and the like are sent to the server 102, the control section 131 of the server 102 generates a patient list in which each piece of information is mutually associated, and the patient list is stored in the external storing apparatus 132 of the server 102 or the like. Incidentally, the patient information, the radiography information, and the like may be transmitted from the various kinds of information reading apparatus, such as the input operating section 133 of the server 102 and an ID card reader, a terminal apparatus, which is installed in a consultation room or the like and is connected to the network 108, and the like in addition to being input from the consoles 107.

At the time of performing the radiography of a radiation image, a radiological technician first goes to the console 107*a*, which is associated with the radiographing room 150 where the radiography is performed, and refers to the patient list stored in the server 102 through the network 108 to make the display section 117 of the console 107*a* display the patient list. Then, the radiological technician selects a patient 111 to be radiographed in the patient list, and the radiography region and the like of the patient 111 as the occasion demands. When a plurality of radiation image detectors 106 is installed in the radiographing room 150, the radiological technician furthermore selects and inputs the radiation image detector 106 to be used for the radiography among the radiation image detectors 106 installed in the radiographing room 150 with the input operating section 118.

Next, the server 102 transmits the patient information and the radiography information to the console 107 and the radiation radiating operation apparatus 104. The patient information and the radiography information are suitably displayed on the display section 117 of the console 107, and the radiological technician confirms these pieces of information while performing the radiography of the radiation image.

The radiation radiating operation apparatus 104 controls the radiation tube 109 of the radiation image radiographing apparatus 103 on the basis of a tube voltage value, a radiation quantity, and the like, which are included in the received radiography information, and the radiation image radiographing apparatus 103 radiates radiations to the patient 111 under these conditions.

At this time, the radiation image detector 106 is inserted into a position between the bed 112 (disposed below the detector 106) and the patient 111 (disposed above the detector 106) to detect the quantity of the radiations that has transmitted the patient 111, and converts the detect radiations into an electric signal to obtain the radiation image information based on the predetermined detection result. Then the radiation detector stores the radiation image information into the image storing section 125.

Moreover, the radiation image information obtained by the radiation image detector 106 is transmitted by the control section 121 to the console 107*a* associated with the radiation image detector 106 as the console 107 operating the radiation image detector 106 at the time of the radiography in the state of being associated with the detecting apparatus ID of the radiation image detector 106 used for the radiography.

The control section 114 of the console 107*a* generates a displaying image on the basis of the radiation image information, and performs the association of the patient information with the radiation image information of the radiation image detector 106 to transmit the radiation image information including the displaying image to the server 102 through the network 108 in the state of being associated with the patient information.

The server 102 associates the sent radiation image information with the patient list to store them into eh external storing apparatus 132.

Moreover, the control section 114 of the console 107*a* makes the display section 117 display the generated displaying image.

If another part of the like of the same patient is furthermore radiographed in the same radiographing room 150, the radiological technician again makes the display section 117 of the console 107*a* display the patient list. Then, the radiological technician selects the radiography region or the like in the radiography at the second time.

When the radiography has been performed similarly at the first time, the radiation image information is stored in the image storing section 125, and is transmitted by the control section 121 to the console 107*a* associated with the radiation image detector 106 as the console 107 operating the radiation image detector 106 at the time of the radiography in the state of being associated with the detecting apparatus ID of the radiation image detector 106 used for the radiography.

The control section 114 of the console 107*a* performs the association of the patient information with the radiation image information by the radiation image detector 106, and generates displaying image. Then, the control section 114 transmits the radiation image information associated with the patient information to the server 102. The server 102 associates the sent radiation image information with a patient list to store it into the external storing apparatus 132, and performs the retrieval of whether the radiation image information coinciding with the patient information associated with the sent radiation image information is stored in the external storing apparatus 132. In the case of the present embodiment, as a result of the retrieval, the displaying image among the pieces of radiation image information obtained by the radiography of the patient at the first time is transmitted to the console 107*a* as the one coinciding with the patient information.

Incidentally, the timing at which the control section 131 of the server 102 performs the retrieval of whether the radiation image information coinciding with the patient information to be radiographed under the operation of the console 107*a* exists among the pieces of radiation image information stored in the external storing apparatus 132 is not limited to the timing when the radiation image information is sent from the console 107*a*. The retrieval may be performed, for example, as follows: at the time when a radiological technician selects the same the patient 111 to be radiographed, a radiography region, and the like, in the patient list, the selection signal is sent to the server 102, and the retrieval is performed to send the displaying image selected as a result of the retrieval is sent to the console 107*a*.

The control section 114 of the console 107*a* makes the display section 117 display the displaying image generated on the basis of the radiation image information radiographed at the second time. At this time, the displaying image obtained by the radiography at the first time is displayed in juxtaposition on the display section 117, and the radiological technician performs the judgment of whether the subject image is properly detected by the radiation image detector 106, and the necessity of re-radiography by confirming the two displaying images.

Moreover, if the radiation image detector 106 is moved to another radiographing room 150 to radiograph another part of the same patient furthermore, the detecting apparatus ID of the radiation image detector 106 is first registered in the console 107*b* managing the radiographing room 150 to be associated with the console 107*b* at the time of installing the radiation image detector 106 into the radiographing room 150. The patient list is then displayed on the display section 117 of the console 107*b*, and a radiological technician selects the radiography region or the like in the radiography of the patient 111 at the third time.

When the radiography has been performed similarly at the first time and the second time, the radiation image information is stored in the image storing section 125, and the radiation image information is transmitted by the control section 121 to the console 107*b* associated with the radiation image detector 106 as the console 107 operating the radiation image detector 106 at the time of radiography in the state of being associated with the detecting apparatus ID of the radiation image detector 106 used for the radiography.

The control section 114 of the console 107*b* performs the association of the patient information with the radiation image information by the radiation image detector 106, and generates displaying image to transmit the radiation image information associated with the patient information to the server 102. The server 102 associates the sent radiation image information with the patient list to store the radiation information into the external storing apparatus 132. Moreover, the control section 131 of the server 102 performs the retrieval of whether the radiation image information coinciding with the patient information associated with the radiation image information sent from the console 107*b* exists among the pieces of radiation image information stored in the external storing apparatus 132. If there is the radiation image information coinciding with the patient information, the control section 131 transmits the displaying image to the console 107*b*. In the present embodiment, the radiation image information obtained by the radiography of the patient at the first time and the second time is treated as the one coinciding with the patient information as the result of the retrieval, and the displaying image of the radiation image information is transmitted to the console 107*b*.

The control section 114 of the console 107*b* makes the display section 117 display the displaying image generated from the radiation image information obtained by the radiography at the third time. Moreover, the display section 117 displays the displaying images, which have been sent from the server 102, by the radiography at the first time and the second time together with the displaying image radiographed at the third time in juxtaposition. The radiological technician performs the judgment of whether the subject image has been properly detected by the radiation image detector 106 and the necessity of re-radiography by confirming the three displaying images.

Furthermore, if only the patient and the radiological technician move to another radiographing room 150 to radiograph another part by the radiation image detector 106 that is different from those of the radiography at from the first time to the third time and is associated with the console 107*c* managing the radiographing room 150 of the moving destination, the radiological technician makes the display section 117 of the console 107*c* display the patient list, and selects the radiography region or the like for the radiography of the patient 111 at the fourth time in the patient list.

When the radiography has been performed similarly to the radiography at from the first time to the third time, radiation image information is stored in the image storing section 125, and is transmitted by the control section 121 to the console 107*c* associated with the radiation image detector 106 as the console 107 operating the radiation image detector 106 at the time of the radiography in the state of being associated with the detecting apparatus ID of the radiation image detector 106 used for the radiography.

The control section 114 of the console 107*c* performs the association of the patient information with the radiation image information of the radiation image detector 106, and generates a displaying image to transmit the radiation image information associated with the patient information to the server 102. The server 102 associates the sent radiation image information with the patient list to store the associated radiation image information into the external storing apparatus 132. Moreover, the control section 131 of the server 102 performs the retrieval of whether the radiation image information coinciding with the patient information associated with the radiation image information sent from the console 107*c* exists among the pieces of radiation image information stored in the external storing apparatus 132. If the radiation image information coinciding with the patient information exists, the control section 131 transmits the displaying image to the console 107*c*. In the present embodiment, the radiation image information obtained by the radiography of the patient at from the first time to the third time is regarded as the radiation image information coinciding with the patient information as the result of the retrieval, and the displaying image of the radiation image information is transmitted to the console 107*c*.

The control section 114 of the console 107*c* makes the display section 117 display the displaying image generated from the radiation image information obtained by the radiograph at the fourth time. Moreover, the displaying images by the radiography at from the first time to the third time, which images have been sent from the server 102, are displayed on the display section 117 in juxtaposition with the displaying image of the radiography at fourth time. The radiological technician judges whether the subject image has been properly detected by the radiation image detector 106 and the necessity of re-radiography by confirming the four displaying images.

If the subject image has been properly detected and re-radiography is unnecessary as the result of the judgment of whether the subject image has been properly detected and the necessity of re-radiography, then the radiological technician inputs the effect of the performance of the proper radiography with the input operating section 118. When the input of the performance of the proper radiography has been performed, the control section 114 of the consoles 107 transmits a signal indicating the properness of the radiography to the server 102. After that, the original image information is suitably output from an outputting machine such as a printer or a monitor after the image processing by the server 102, and is supplied to the diagnosis of a doctor as a radiation image. On the other hand, the displaying image is deleted by the control section 114.

Moreover, the control section 114 transmits a signal indicating the properness of the radiography state of the radiation image and a deletion instruction signal instructing the deletion of the radiation image information stored in the radiation image detector 106 to the radiation image detector 106. When the control section 121 of the radiation image detector 106 receives these signals, the control section 121 deletes the radiation image information from the image storing section 125, and ends the radiography by the radiation image detector 106. Then, in this case, the display section 117 of the consoles 107 suitably displays the patient information, the radiography information, and the like, of the next radiography.

On the other hand, if a signal indicating that the subject image has not been properly detected and the necessity of re-radiography exists is input from the input operating section 118, the control section 121 deletes the original image information and the displaying image, and transmits an instruction instructing re-radiography to the radiation radiating operation apparatus 104. Hereby, re-radiography is performed, and the radiation image information obtained by the radiation image detector 106 is transmitted to the console 107 that has operated the radiation image detector 106 at the time of radiography similarly to the case mentioned above.

The control section 114 of the console 107 associates the radiation image information with the patient information and the like to transmits the associated information to the server 102, and generates a displaying image having a smaller information quantity than that of the original image information on the basis of the radiation image information to make the display section 117 display the generated displaying image.

If an input indicating that the subject image has been properly detected and there is no necessity of re-radiography is input from the input operating section 118, the control section 114 of the console 107 deletes the displaying image, and transmits a signal indicating that the radiography state of the radiation image has been proper and a deletion instruction signal instructing the deletion of the radiation image information stored in the radiation image detector 106 to the radiation image detector 106 similarly to the case mentioned above. And the control section 114 ends the series of radiography operations.

As described above, by the radiation image radiographing system 101 according to the present embodiment, the whole radiation image information obtained by radiating the patient is transmitted to the associated console 107 operating the radiation image detector 106 at the time of the last radiograph of the patient, and the displaying image is displayed on the display section of the consoles 107. Consequently, even if any of the consoles 107 performs the inputs of patient information and radiography information and the association of the radiation image detector 106 with the console 107, the console 107 located in the vicinity of the radiographing room 150 where a radiological technician is currently performs radiography operations can confirm the suitability of the whole radiography of the radiographed images, and the radiological technician can instantly and surely weigh whether the subject image has been properly detected and can judge the suitability of the radiation image without moving to a position distant from the radiographing place. Consequently, the operationality at radiography can be improved.

Incidentally, in the present embodiment, the timing when the control section 131 of the server 102 retrieves the radiation image information associated with the same patient information from the external storing apparatus 33 is the time when the radiation image information associated with the patient information is sent from the console 107. But, the timing of the retrieval is not limited to that time. For example, the timing may be determined as follows: if the patient to be radiographed and the like are selected from the patient list as the setting before radiography, then the information is transmitted to the server 102, and the control section 131 performs the retrieval.

Moreover, in the present embodiment, the plurality of displaying images sent to the console 107 is displayed on the display section 117 of the console 107 side by side, but the method of the display is not limited to the above one. For example, each displaying image may be suitably changed to be displayed on the display section 117.

Moreover, in the present embodiment, after the radiation image information based on a detection result by the radiation image detector 106 has been transmitted to the console 107 corresponding to the radiation image detector 106, a displaying image is generated in the control section 114 of the consoles 107, but the displaying image generating means for generating the displaying image is not limited to the case where it is the control section 114 of the consoles 107.

For example, if the radiation image detector 106 is the cassette shaped FPD as the present embodiment, then the displaying image may be generated by the control section 121 of the radiation image detector 106. In this case, both of the original image information and the displaying image radiation that have been generated by the control section 121 of the image detector 106 may be sent to the console 107 by the communication means that is wireless or the like, or may be sent to the server 102. Furthermore, only the displaying image may be sent to the console 107, and the original image information may be sent to the server 102. Moreover, the original image information may be stored in the image storing section 125 of the radiation image detector 106, and only the displaying image may be sent to the console 107. In this case, the system may be configured as follows: when a signal indicating that the radiography state of the radiation image is proper is sent from the console 107 to the radiation image detector 106, the original image information is transmitted to the console 107 or the server 102. Moreover, the system may be configured so that the radiation image information obtained by the radiation image detector 106 may be directly sent to the server 102, and that the server 102 may generate a display image besides the original image information.

Moreover, in the present embodiment, after all of the detection results detected by the radiation image detector 106 are sent to the console 107, the detection results are transmitted to the server 102, the detection results may be directly sent from the radiation image detector 106 to the server 102. Moreover, if the radiation image detector 106 generates the displaying image from the detection result, only the displaying image may be transmitted to the console 107, and the original image information may be stored in the image storing section 125 of the radiation image detector 106; or only the displaying image may be transmitted to the console 107, and the original image information may be transmitted to the server 102. If the original image information is stored in the image storing section 125 of the radiation image detector 106, then, when re-radiography becomes unnecessary after that, the control section 114 of the consoles 107 suitably transfers the detection results pertaining to the radiography, which results are stored in the radiation image detector 106, to the server 102 or the console 107 through the communication section 119, and after that a signal is transmitted to delete the detection results.

Incidentally, in the present embodiment, a patient list is generated in the control section 131 of the server 102, but the main component of the generation of the patient list is not limited to the control section 131. For example, the patient list may be treated as follows: the patient list is generated in the control section 114 of the console 107, and the generated patient list is sent from the console 107 to the server 102. Then, the patient list is stored in the external storing apparatus 132 of the server 102, and the patient list is transmitted from the server 102 to each of the consoles 107 to be shared by them.

Incidentally, in the present embodiment, after a radiation image detector 106 has been once associated with a certain console 107, if the radiation image detector 106 is newly associated with another console 107 because of moving to another radiographing room 150, then the association of the radiation image detector 106 with the console 107 that has been previously associated is released. But, if a new association of the radiation image detector 106 with another console is formed owing to the movement to another radiographing room 150, then the previously formed association may not be released also, and a plurality of associations may be duplicated.

In this case, for example, by associating the radiation image obtained by the radiation image detector 106 with the console ID of the console 107 operating the radiation image detector 106 at the time of the radiography, the radiation image is transmitted only to the console 107 having the console ID. Hereby, the image can be transmitted only to the console 107 that has operated the radiation image detector 106 at the time of the radiography, and after the radiography, the image can be confirmed immediately in the vicinity of the radiographing room 150. Consequently such a configuration is convenient.

Moreover, in the present embodiment, the radiation image radiographing apparatus 103 is operated by the radiation radiating operation apparatus 104, but the radiation image radiographing apparatus 103 may be configured to be operated by the consoles 107 or the like. In this case, it is unnecessary to provide the radiation radiating operation apparatus 104, and the system configuration can be simplified.

Because a radiation image detector to which a radiation image radiographing system according to the present invention is applied can automatically control the state of power supply according to the operation status of an associated console, the troubles of the operation for starting the radiation image detector and the time of waiting the start-up thereof can be removed when radiography is desired to be performed urgently, and the operationality at the time of radiography can be improved. Moreover, it is possible to prevent that unnecessary exposed to radiation is given to a patient by an error in operation such as the misuse of the radiation image detector that is not started, which obliges the patient to receive re-radiography.

In particular, if the state of power supply is controlled to suppress the power consumption of the radiation image detector when the console is not started, then the radiation image detector can be set in a power saving mode, in which the power consumption is suppressed, when the console is not started, that is, when no radiography is performed, and useless power consumption can be reduced.

Consequently, the radiation image radiographing system according to the present invention is especially fitted to a medical scene where urgent radiography is performed.

EXPLANATION OF REFERENCE NUMERALS

1, 101: radiation image radiographing system
2, 102: server
3, 104: radiation radiating operation apparatus
4, 105: base station
5, 106: radiation image detector
6, 107 (107*a*, 107*b*, 107*c*): console
7, 108: network
10: radiation radiating apparatus
11, 150: radiographing room
16: scan and drive circuit (radiation image detector)
17: signal reading circuit (radiation image detector)
18, 125: image storing section (radiation image detector)
19: built-in power supply (radiation image detector)
21: power supplying means (radiation image detector)
22: terminal (radiation image detector)
23: association detecting means (radiation image detector)
24, 126: communication section (radiation image detector)
25: indicator (radiation image detector)
27, 36, 121: control section (radiation image detector)
28: control apparatus (radiation image detector)
29, 35, 114: control section (console)
30: control apparatus (console)
31, 118: input operating section (console)
32, 117: display section (console)
33: communication section (console)
34: charging apparatus
40: detecting means
41: releasing means
103: radiation image radiographing apparatus
115: RAM (console)
116: ROM (console)
120: bus (console)
122: RAM (radiation image detector)
123: ROM (radiation image detector)
124: plane detecting section (radiation image detector)
127: power supply section (radiation image detector)
128: input operating section (radiation image detector)
129: bus (radiation image detector)
130: rechargeable battery
131: control section (server)
132: external storing apparatus (server)
133: input operating section (server)
134: display section (server)
135: bus (server)

The invention claimed is:

1. A radiation image radiographing system comprising:

a portable cassette shaped radiation image detector to detect an applied radiation to obtain image information;

a plurality of consoles for operating the radiation image detector;

an associating section to perform association with one of the plurality of consoles for operating the radiation image detector at radiographing;

a releasing section to release the association with the console associated by the associating section; and a control section to allow the releasing section to release the association with the console associated by the associating section when the associating section associates another console from the plurality of consoles with the radiation image detector.

2. The radiation image radiographing system of claim 1, wherein the radiation image detector includes a power supplying section to control a state of power supply according to an operating status of the console associated by the associating section.

3. The radiation image radiographing system of claim 2, wherein the radiation image detector, as the state of power supply, includes:

a state of being capable of radiography with power consumption necessary for radiographing:

a state of waiting radiography with lower power consumption than in the state of being capable of radiography; and a state of preparing waiting with lower power consumption than in the state of waiting radiography.

4. The radiation image radiographing system of claim 3, wherein the power supplying section changes the state of power supply to the state of being capable of radiography or the state of waiting radiography when it is detected that the console is in operation.

5. The radiation image radiographing system of claim 3, wherein the power supplying section changes the state of power supply to the state of preparing waiting when it is detected that the console is in a halt condition.

6. The radiation image radiographing system of claim 5, wherein the power supplying section changes the state of power supply to the state of waiting radiography after a lapse of predetermined time from changing the state of power supply to the state of being capable of radiography, when any radiography instructions has been received from the console.

7. The radiation image radiographing system of claim 1, wherein the console associated by the associating section includes an informing section to inform a state of power supply of the radiation image detector.

8. The radiation image radiographing system of claim 1, wherein the radiation image detector is a cassette type flat panel detector.

9. The radiation image radiographing system of claim 1, wherein the radiation image detector includes: detecting section to detect the progress of an operation based on an instruction from the console associated by the associating section; and the control section to allow a power supplying section to control a state of power supply when completion of the operation according to the instruction of the console associated by the associating section is detected.

10. The radiation image radiographing system of claim 9 wherein the control section allows the releasing section to release the association with the associated console when the detecting section detects the completion of the operation according to the instruction of the associated console.

11. The radiation image radiographing system of claim 10, wherein the control section enables the association with the another console when the releasing section releases the association with the console associated by the associating section.

* * * * *